United States Patent [19]
Christensen et al.

[11] Patent Number: 6,085,577
[45] Date of Patent: Jul. 11, 2000

[54] SURFACE TENSION MEASUREMENT IN A PRESSURIZED ENVIRONMENT

[75] Inventors: Tanya C. Christensen, Gilbert, Ariz.; Alexander F. Teichmann, Heitersheim, Germany; Victor P. Janule, Gilbert, Ariz.

[73] Assignee: Chem-Dyne Research Company, Mesa, Ariz.

[21] Appl. No.: 09/043,952

[22] PCT Filed: Oct. 3, 1996

[86] PCT No.: PCT/US96/15923

§ 371 Date: Jul. 16, 1998

§ 102(e) Date: Jul. 16, 1998

[87] PCT Pub. No.: WO97/13138

PCT Pub. Date: Apr. 10, 1997

[51] Int. Cl.[7] .................................................. G01N 13/00
[52] U.S. Cl. .................................................. 73/64.51
[58] Field of Search ............................. 73/64.51, 64.48, 73/64.49, 64.52

[56] References Cited

U.S. PATENT DOCUMENTS

| | | | |
|---|---|---|---|
| 3,426,584 | 2/1969 | Smith | 73/64.51 |
| 3,765,227 | 10/1973 | Campbell et al. | 73/64.51 |
| 4,416,148 | 11/1983 | Klus et al. | 73/64.51 |
| 4,527,421 | 7/1985 | Miller, Jr. | 73/64.51 |
| 5,426,976 | 6/1995 | McHardy et al. | 73/202 |

OTHER PUBLICATIONS

Fainerman, et al, Colloid and Polymer Science, Jun. 1, 1994, v. 272 n. 6, pp 731–739.

*Primary Examiner*—Hezron Williams
*Assistant Examiner*—Jay L. Politzer
*Attorney, Agent, or Firm*—Kremblas, Foster, Millard & Pollick

[57] ABSTRACT

Method and apparatus for measuring the surface tension of a liquid inside a vessel (2), reactor, or inside a section of flow-through process pipe that is pressurized above normal ambient pressure, up to but not limited, to 100 psig (7000 kPa), includes a pair of tubes (2,3) having a small and large orifice in a modular probe assembly that allows the probes to be positioned at selected and variable distances below the surface of the liquid. A high pressure source (4) provides an inert nitrogen or process gas through a pressure regulator (5) to the input of two or three mechanical or electronic mass flow controllers (6,7,8), powered by an external power supply (9), which control the bubble rate at each orifice through manual adjustments, or electronic set points determined by a computer software program, independent of the pressure in the vessel, reactor, or flow-through process pipe. One or more differential pressure transducers (10,11) measure the pressure of bubbles being formed and released from the two orifices. A transducer demodulator circuit (12) converts the resulting fluctuating pressure signal directly to an equivalent fluctuating electrical DC voltage signal. This signal is input to a (13) computer using one or more plug-in analog input/output computer interface circuit boards (14). A software program tracks the differential waveform and captures the maximum differential bubble pressure which is directly proportional to fluid surface tension. A temperature probe (15) and/or other commercially available probe (such as conductivity, viscosity, or density) is immersed at the same level as the orifices to measure liquid temperature, and/or other process parameters. A pneumatic damper (16) smoothes the large orifice signal in the single transducer apparatus (FIG. 1), whereas in a two transdcuer apparatus the average maximum values of the two individual, undampened, pressure signals are electronically substracted to provide the maximum differential bubble pressure which is directly proportional to fluid surface tension.

10 Claims, 21 Drawing Sheets

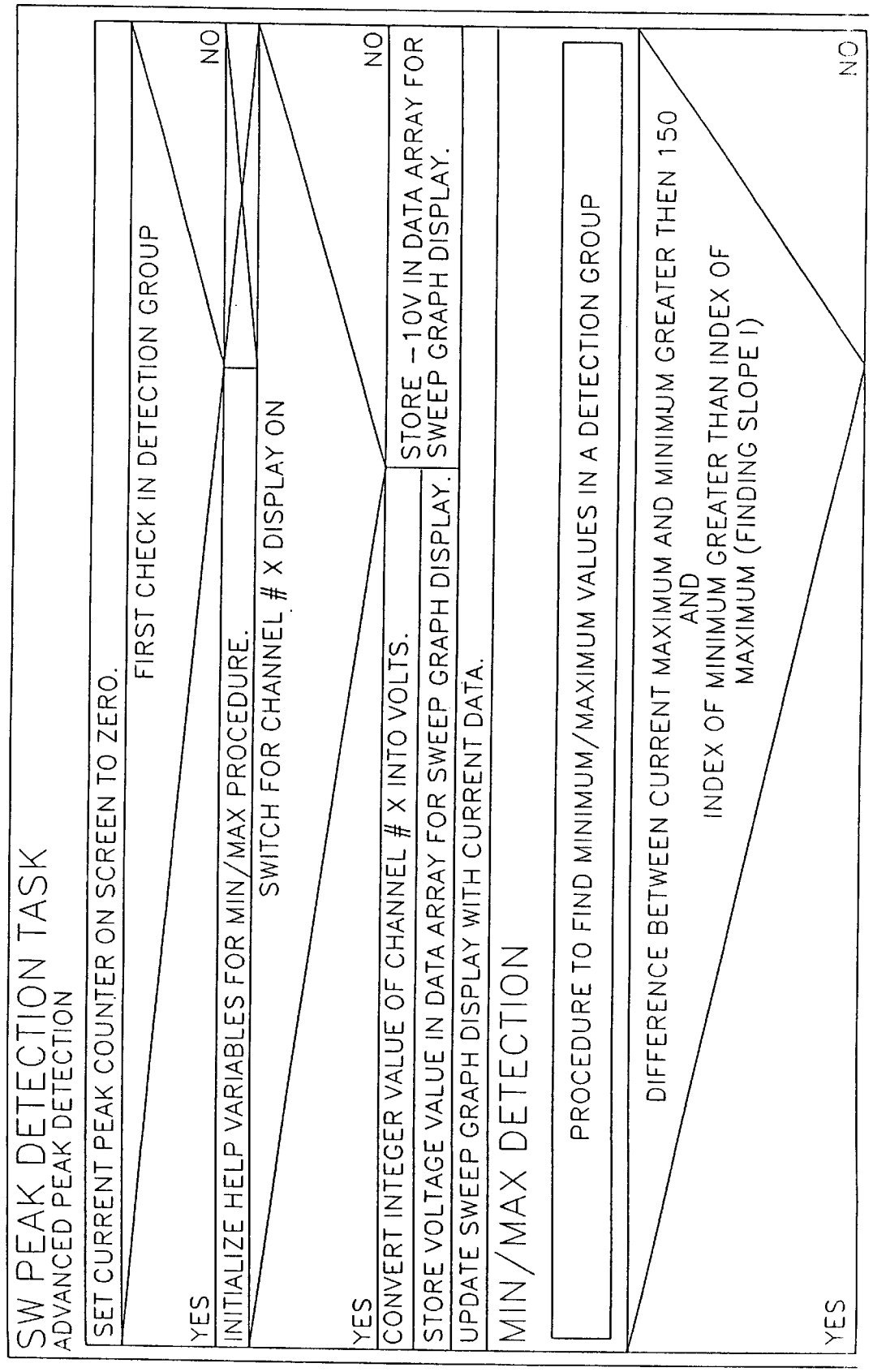

FIG-17

SORT PEAK AMPLITUDES.

SORT VALUES IN SPECIFIED ANALYZATION ARRAY BY SIZE, USING THE BUBBLE SORT METHOD.

SURFACE TENSION MEASUREMENT IN A PRESSURIZED ENVIRONMENT

BACKGROUND OF THE INVENTION

The maximum differential bubble pressure method, employing two orifices of different diameters immersed in the body of a fluid was tested and proven to be adaptable for measuring in a pressurized environment over fifteen years ago as described in U.S. Pat. 4,416,148, up to a nominal 10 psig pressure, at 25 degrees Celsius. Electronic hardware peak detection for fluid surface tension measurement with the modified maximum differential bubble pressure technique has proven satisfactory for non-viscous fluids, and fluids tested under non-pressurized conditions. Hardware peak detection is limited to transducer output signals that are unipolar (positive) in value, nominally between 0 to 5, or 0 to 10 Volts DC. Hardware peak detector circuits will, however, false trigger on a zero crossing.

Electronic hardware peak detection circuits have a number of further limitations when certain pneumatic conditions change the differential pressure waveform by generating false peaks that trigger the hardware peak detector. Hardware peak detectors can false trigger (see FIG. 4) on pressure signal fluctuations that are caused by capillary action when 0.1 mm I.D. and larger orifices are used in the small orifice position. As the viscosity of a liquid increases, there is increased hydrodynamic resistance of the liquid against a moving bubble. Very viscous fluids, and fluids with high suspended solids concentration, cause electronic peak detectors to false trigger. Greater pneumatic pressures required to overcome the increased hydrodynamic resistance at an orifice can cause unstable or noisy waveforms.

Lowering the amplitude of the differential pressure waveform will reduce the amplitude of the false peaks proportionately so that the electronic hardware peak detector no longer trigger on the false peaks; however, this can lower the amplitude of the waveform in lower surface tension fluids to the point where they no longer trigger the electronic peak detector. In this situation, it is no longer possible to calibrate the instrument in a low standard calibration fluid, as for example, alcohol.

The electronic hardware peak detector will also false trigger on waveform noise oscillations that result when the measured test fluid is pressurized. Mass flow controllers, required to operate in an increasing pressurized environment, cause a maximum bubble pressure waveform that becomes increasingly unstable between bubbles (FIG. 6). Large oscillations occur following the release of each bubble before the system stabilizes and the next bubble is blown.

In a non-pressurized environment the bubble rate remains constant once the flow rate is set with mass flow controllers. However, in an increasing pressurized environment, although the maximum bubble pressure remains constant and therefore surface tension remains constant, bubble rate will decrease (slow down) with increasing pressure (see FIGS. 4 and 6).

Electronic hardware peak detection circuits are further limited in responding to various amplitude and frequency changes of the maximum bubble pressure waveform and waveform shapes will change as bubble rate is changed, and as fluid viscosity increases. At one bubble per second, the waveform flows a sawtooth configuration (FIG. 4) where a linear positive slope follows the increase in pressure as the bubble is formed up to its maximum bubble pressure point. When a bubble releases there is a sharp drop (negative downslope) followed by a momentary back pressure and capillary action before the pressure equalizes inside the tube and the next bubble begins to form. The positive slope is commonly referred to as the "surface age" of the bubble while the rest is commonly referred to as "dead time" (FIG. 5).

An ideal hardware peak detector should track only the surface age (positive) portion of the sawtooth wave until it reaches a valid maximum, capture that maximum value, trigger a reset signal by detecting the subsequent drop (negative downslope), and then track the next valid peak.

The dead time of a sawtooth waveform is finite and depends on the rheology of the fluid, the diameter and configuration of the orifice, and the pressure characteristics of the mass flow controllers. As bubble rate increases, dead time becomes a greater proportion of the peak-to-peak bubble interval time. At one bubble per second (FIG. 4) the surface age typically is in excess of ninety percent of the bubble interval, while at thirty five or more bubbles per second, the surface age can be less than ten percent of the bubble interval (FIG. 5).

Mass flow controllers are set for a specific flow rate when an instrument is set up and calibrated; however, bubble rate will change if surface tension of the fluid changes, even though flow rate stays fixed. A peak detector must be flexible enough to cover all possible bubble ranges. For example, a flow setting that produces one bubble per second in water, with surface tension in the 70+dynes/cm. range, produces more than three bubbles per second in alcohol, with surface tension typically in the 20 plus dynes/cm range. The waveform amplitude in alcohol is much smaller due to lower surface tension of alcohol. Electronic peak detection circuits lack capability to ignore various noise oscillations and signal combinations as described.

SUMMARY OF THE INVENTION

In the present invention, an advanced software peak detection program is provided to solve problems encountered using hardware peak detection and to allow for accurate surface tension measurement. The resulting software program used in the present invention can be extended, with minor hardware modifications, to the accurate surface tension measurement of viscous fluids and fluids with high solids content in both ambient and under pressurized conditions.

No continuous process instrument for making surface tension measurements under pressure is presently being marketed. There is a need for such an instrument to measure surface tension of pressurized liquefied gases (such as natural gas, freon, and freon replacements), in latex polymerization reactors, and in liquids and thermoplastic materials that are produced or converted under high pressure.

It is therefore an object of this invention to provide an apparatus for determining surface tension of a liquid independent of the pressure environment of the container holding the liquid or the depth of immersion of the probes under the surface of the liquid.

It is another object of this invention to provide a software and hardware means to open the mass flow controller control valve to its full open position to increase the flow through the mass flow controllers to a maximum, in order to purge the probes during the period that a vessel, reactor, or pipe is pressurized, so as to prevent the back flow of liquid into the probes, particularly fluids with high solids concentration that can cause plugging of the probes. This purging capability can also be used as a means to unplug the probes during the normal production cycle, if needed.

It is a further object of this invention to provide a multiple transducer system so that the two sensing orifices are physically decoupled and the maximum bubble pressure peaks from each of the two orifice signals are individually averaged. The maximum average of the signal from the large orifice is electronically subtracted from the maximum average of the signal from the small orifice to provide an extremely accurate maximum differential bubble pressure value, directly proportional to surface tension. In highly viscous fluids the ratio of the bubble rates can be set to make the surface tension value independent of viscosity effects. This is applicable in both non-pressurized and pressurized environments.

It is a still further objective of this invention to provide a flexible, modular, and interchangeable mechanical means for varying the immersion length, orientation, and position of surface tension, temperature, and other similar measurement probes inside a vessel, reactor, or pipe section, both in an ambient and pressurized environment. This mechanical means includes a porous basket at the end of probe which mitigates the effect of shearing or turbulence (which would otherwise be detrimental to the free information of bubbles at the probe orifices) from the flow or mixing of the fluid in the vessel, reactor, or pipe, while at the same time allowing the free, non-turbulent flow of the fluid past the tension orifices and associated temperature or other measurement probes.

Other objects and advantages of the invention will be apparent from the following description, the accompanying drawings and the appended claims.

BRIEF DESCRIPTION OF THE DRAWINGS

FIGS. 14A and 14B together comprise a more detailed software flow diagram of the advanced software peak detection routine of the present invention;

FIG. 17 is a simplified block diagram representing the software routine for sorting values.

DESCRIPTION OF THE PREFERRED EMBODIMENT

Figure 1:
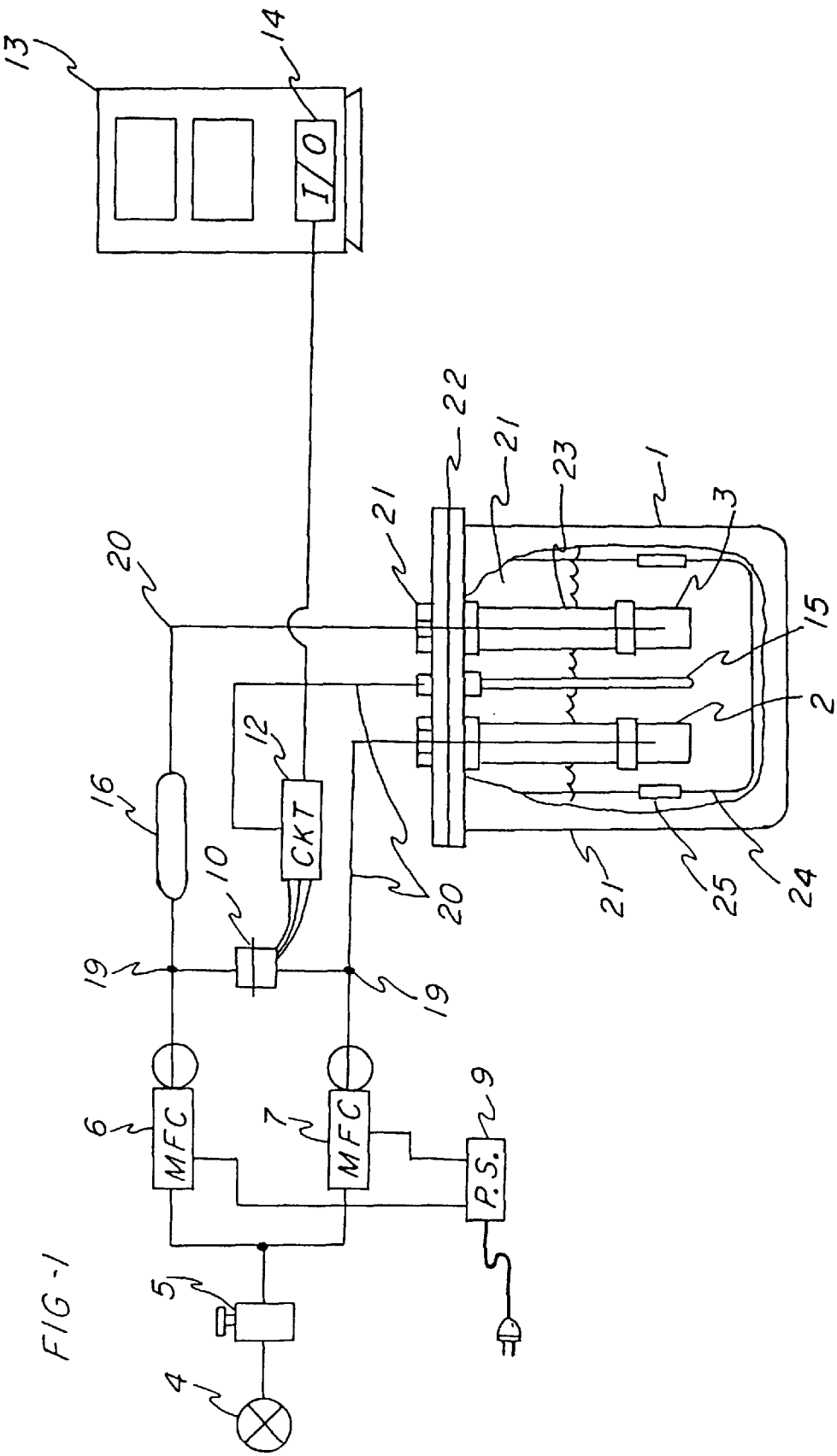
FIG. 1 is a combined pneumatic and electrical block diagram showing the components comprising the preferred embodiment of the invention using a single differential pressure transducer and two mass flow controllers.

Referring to the drawings which illustrate a preferred embodiment of the invention, and particularly to FIG. 1, an apparatus for determining the surface tension of a liquid in a pressurized environment, up to but not limited to 1000 psig (7000 kPa), includes a source of high pressure nitrogen or process gas (4) which is connected through appropriate high pressure tubing, fittings, or hoses to a pressure regulator means (5).

Figure 2:
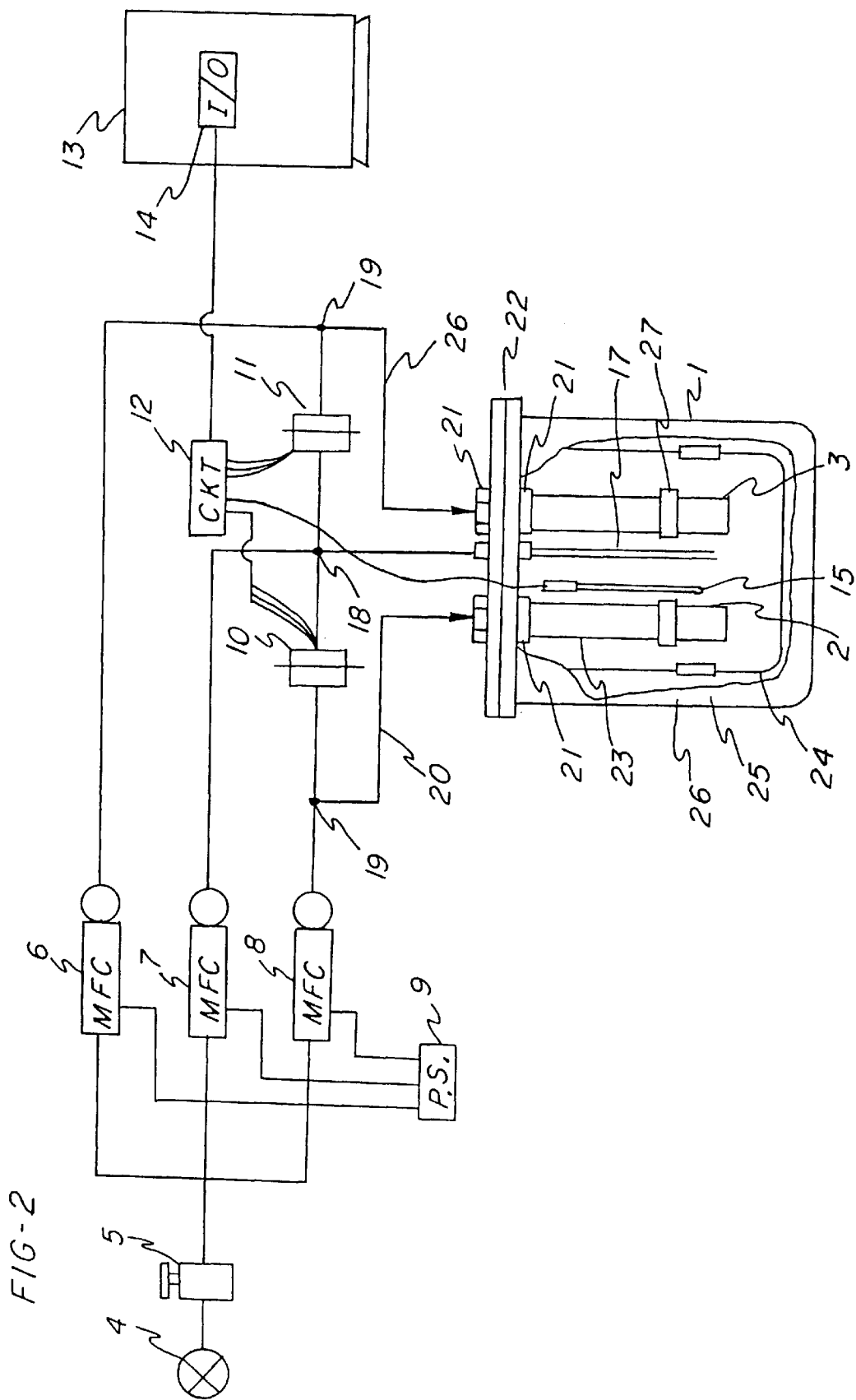
FIG. 2 is a combined pneumatic and electronic block diagram similar to FIG. 1 illustrating the components comprising an alternative arrangement using two differential pressure transducers and three mass flow controllers.
Figure 3:
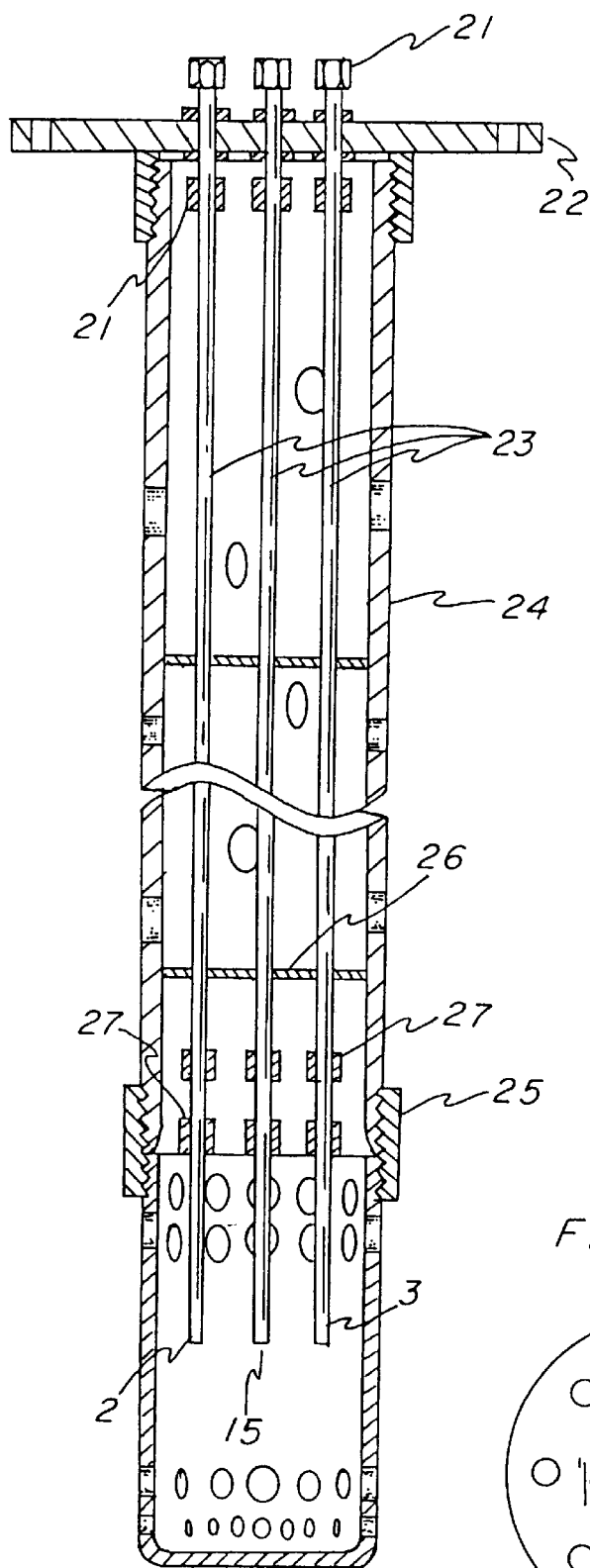
FIG. 3 is a cross sectional view of a modular probe assembly for use in both pressurized and non-pressurized vessels, reactors, or process pipe sections, showing means for using standard and replaceable small and large orifice probes and other process monitoring probes such as temperature and conductivity.
Figure 3B:
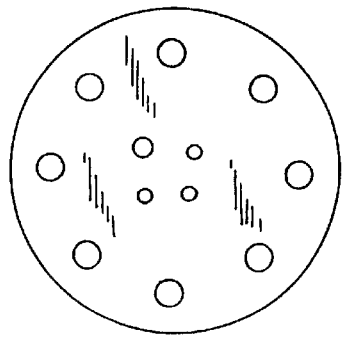
FIG. 3B is a plan view of the probe of FIG. 3.
Figure 3A:
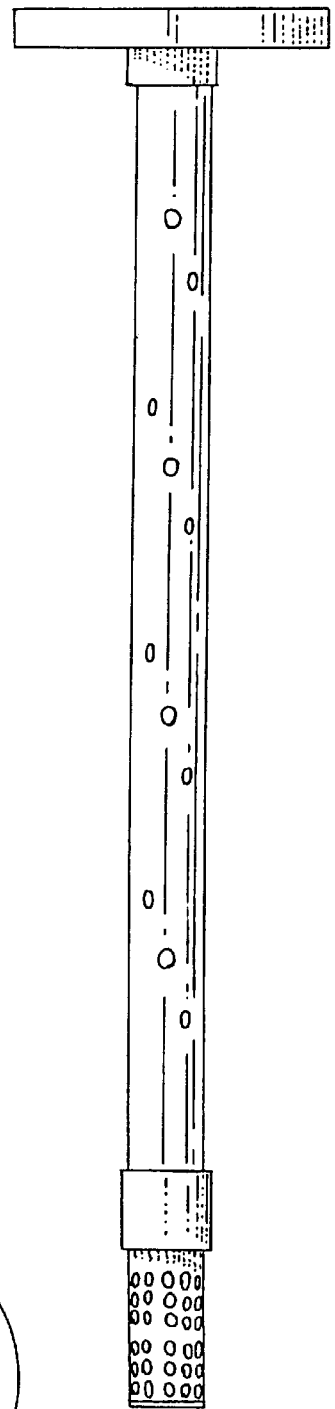
FIG. 3A is a side elevational view of the probe of FIG. 3.
Figure 4:
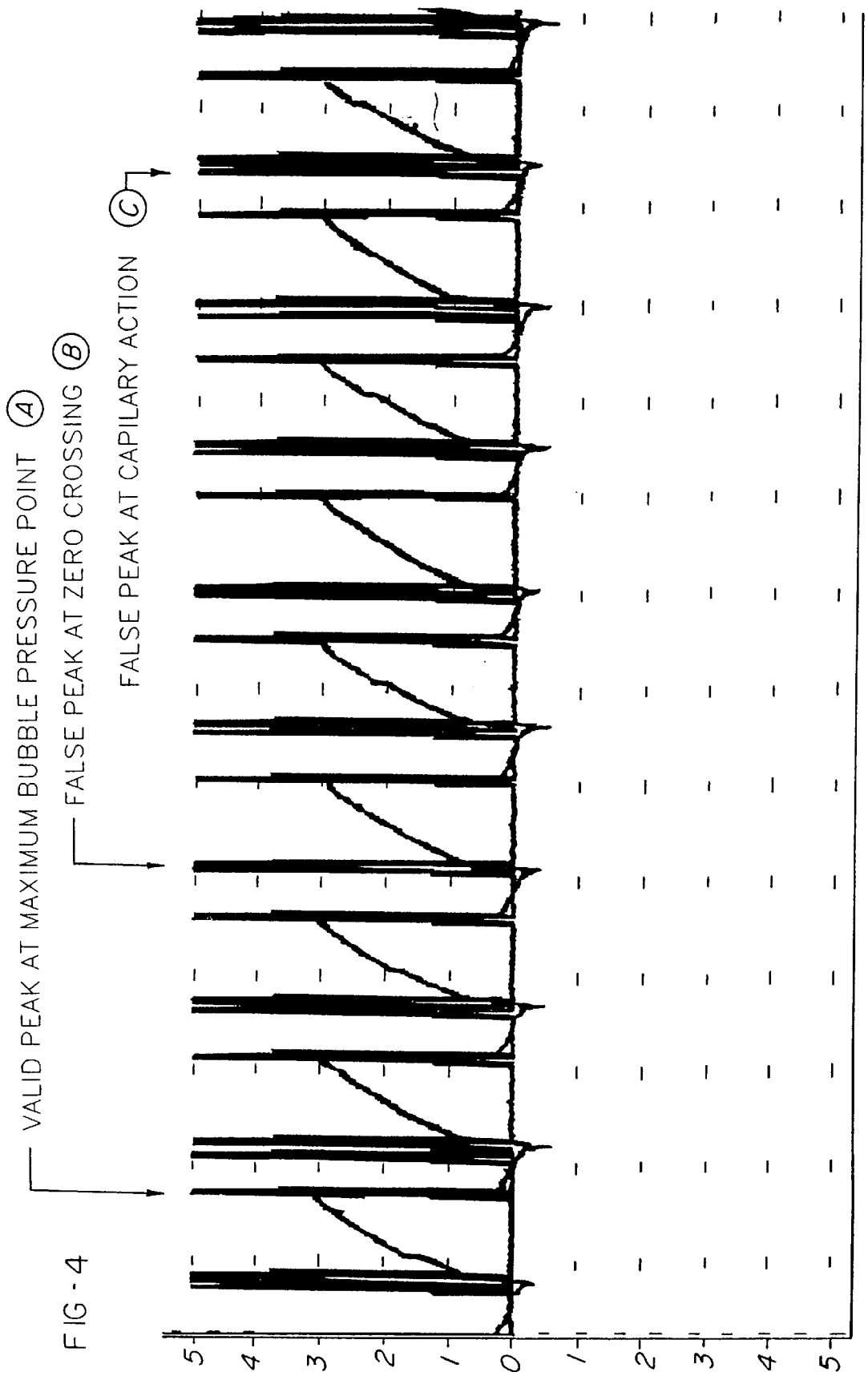
FIG. 4 is a waveform diagram of a normal maximum differential bubble pressure waveform showing three distinct hardware peak detector trigger signals: a valid peak at the maximum bubble pressure point (A); a false peak on a zero crossing (B); and a false peak on a capillary action (C)
Figure 5:
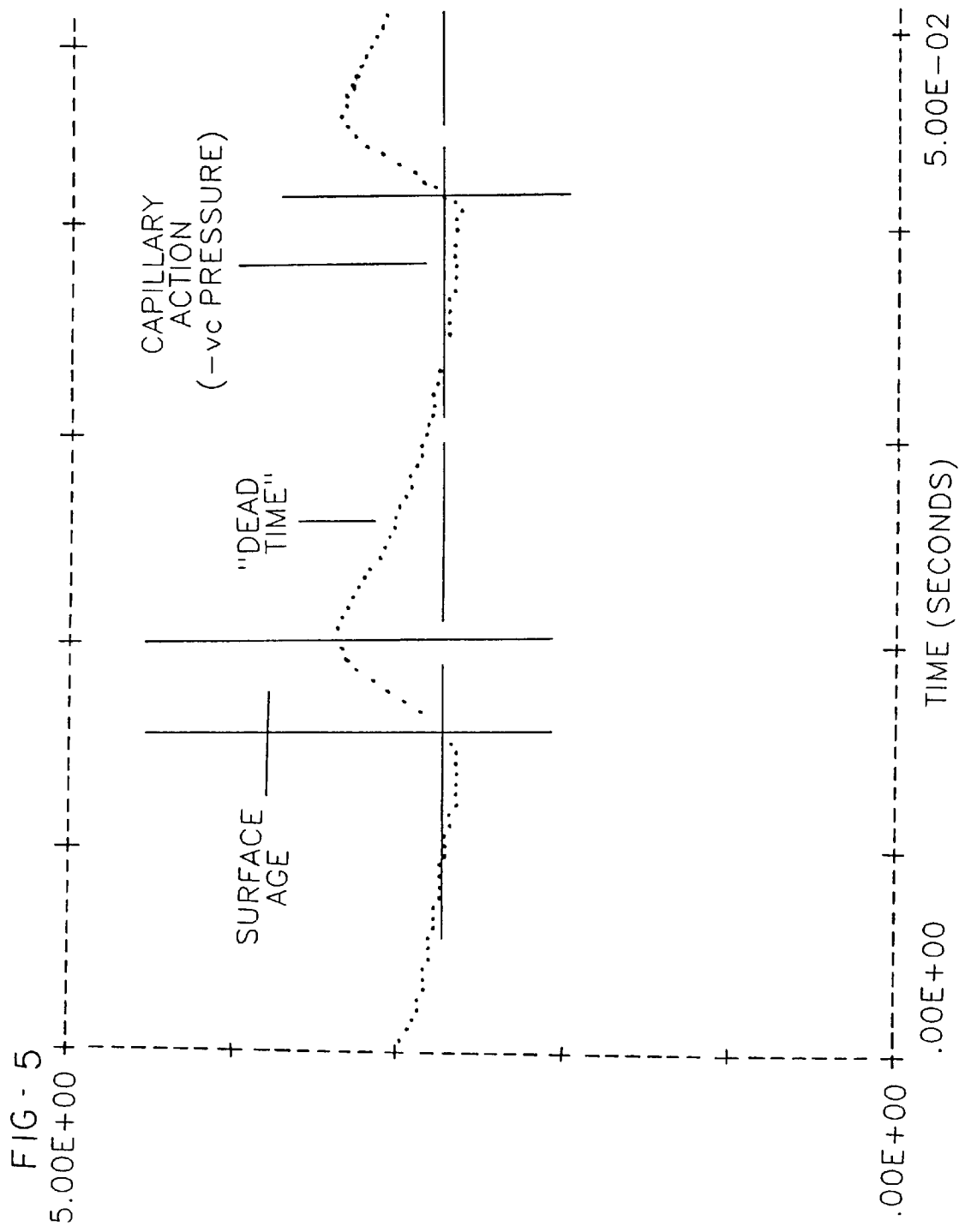
FIG. 5 is a waveform diagram of a normal differential bubble pressure waveform at thirty five bubbles per second showing the surface age and dead time.
Figure 6:
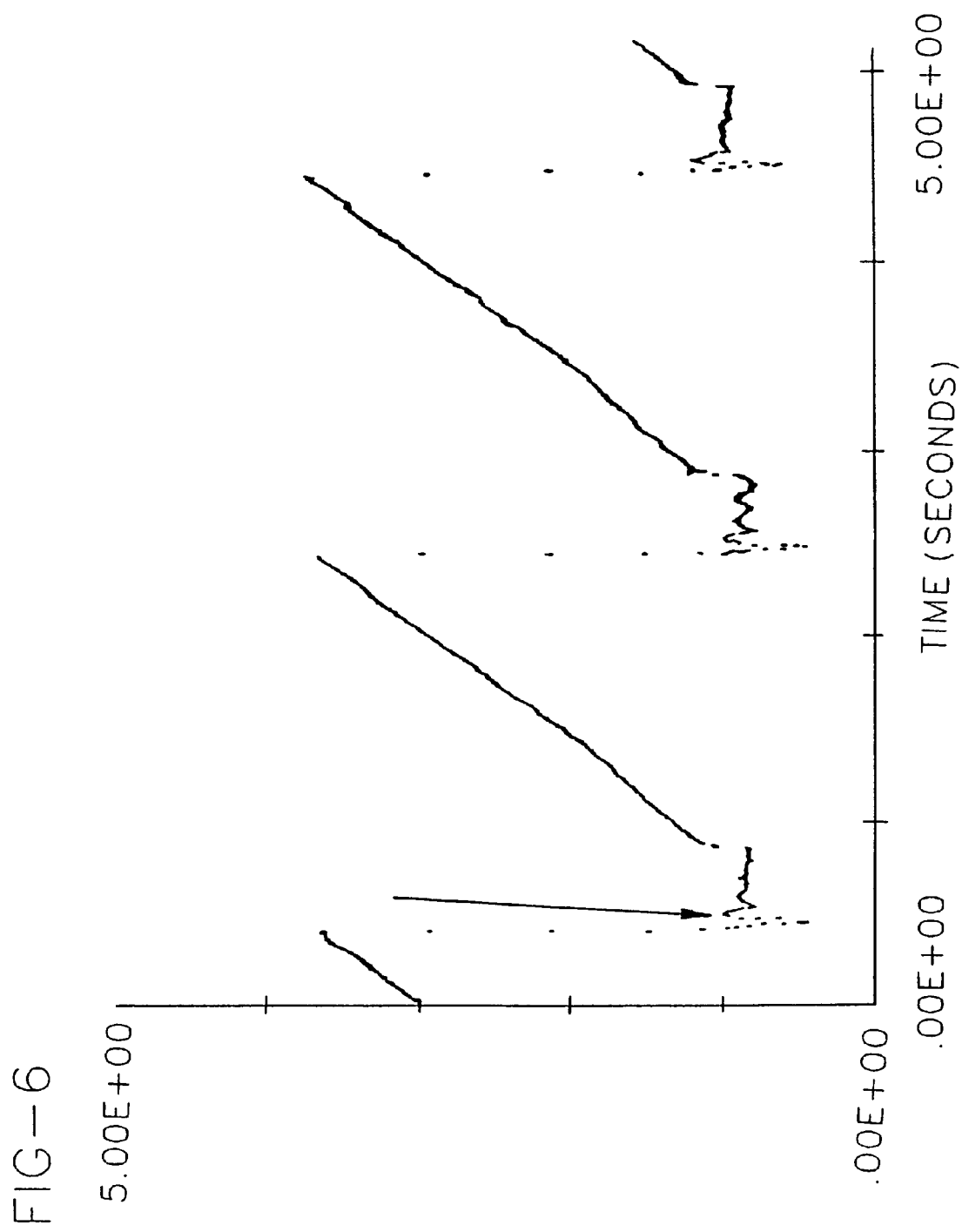
FIG. 6 is a waveform diagram of a normal maximum differential bubble pressure waveform in water under 175 PSIG pressure showing the signal oscillating after each bubble is released.
Figure 12:
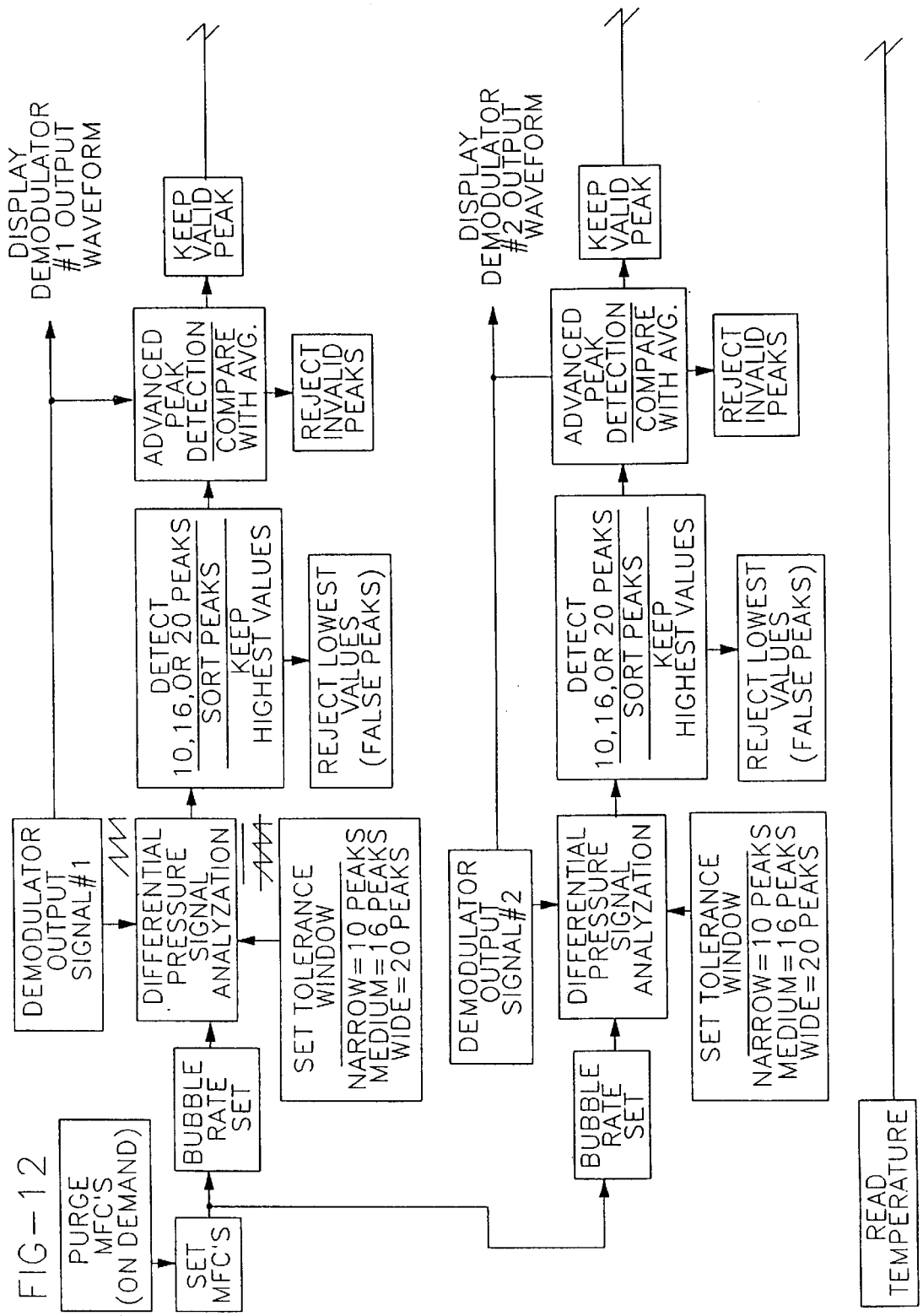
FIGS. 12 and 12A together comprise a system block diagram showing the process for measuring surface using the components shown in FIG. 2.
Figure 12A:
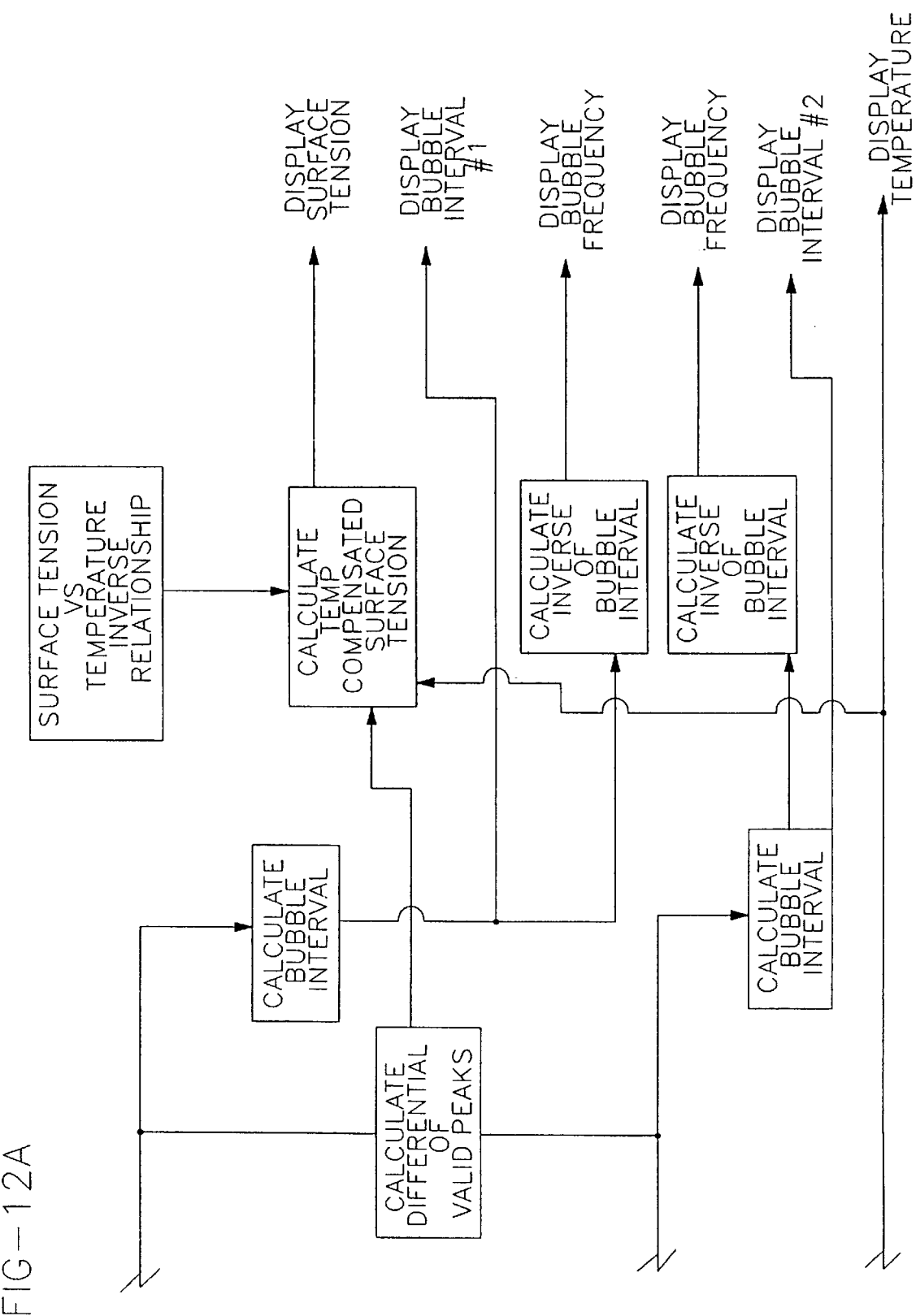
Figure 13:
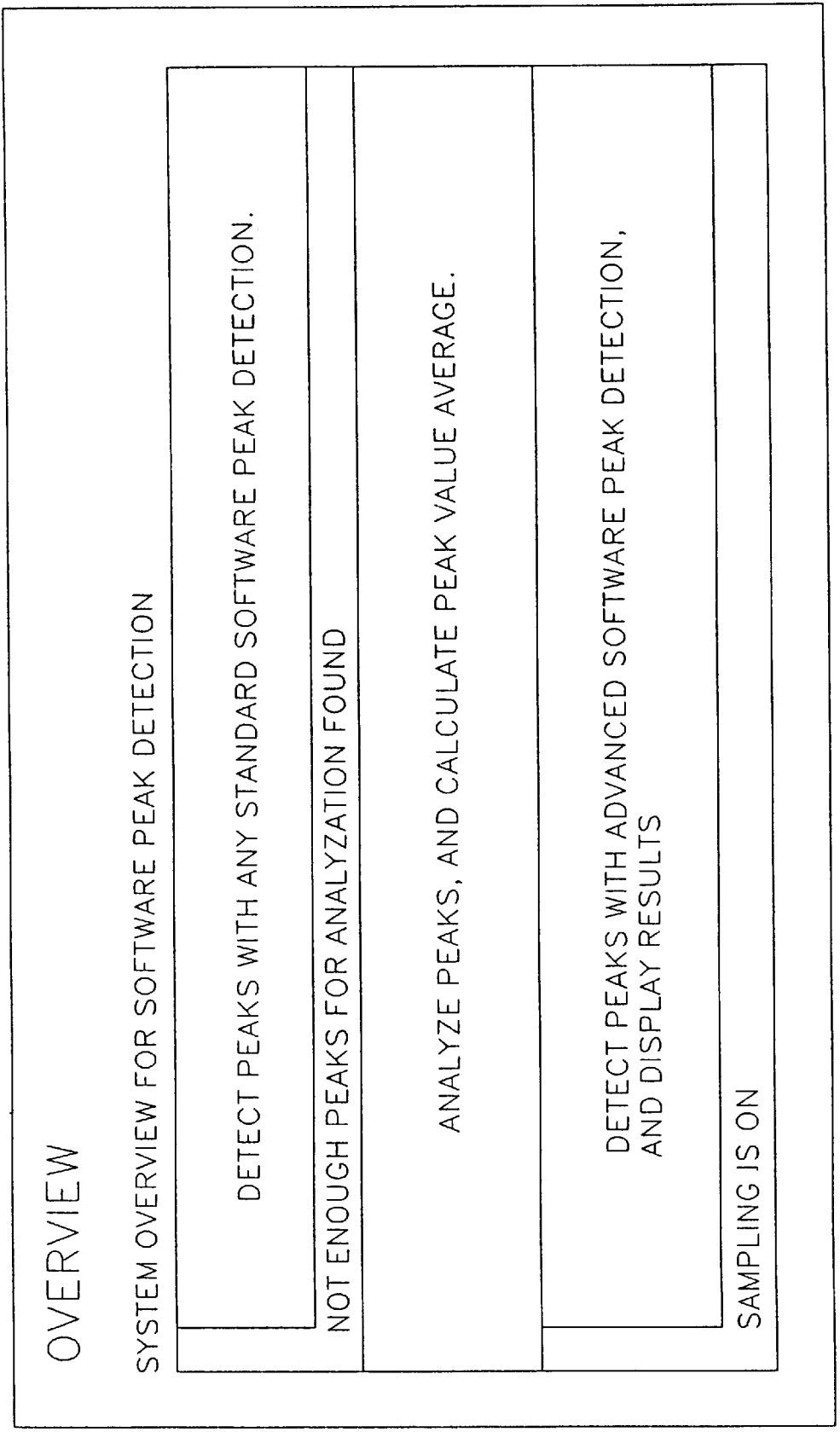
FIG. 13 is a simplified software flowchart showing the overall system for software peak detection.

The invention includes means to accept a high input pressure source and reduce the pressure, as may be necessary to provide a corresponding precise output mass flow control of the process gas, to the probe assembly, using one mass flow controller (mass flow controller) per orifice (6, 7), and where necessary, a third mass flow controller (8) as used in the two transducer (10, 11) scheme as illustrated in FIGS. 2 and 12. The mass flow controllers used in one embodiment of the invention is a MKS Model 1261 rated for constant mass flow in the range from 0 to 100 milliliters (SCCM) per minute.

Figure 11:
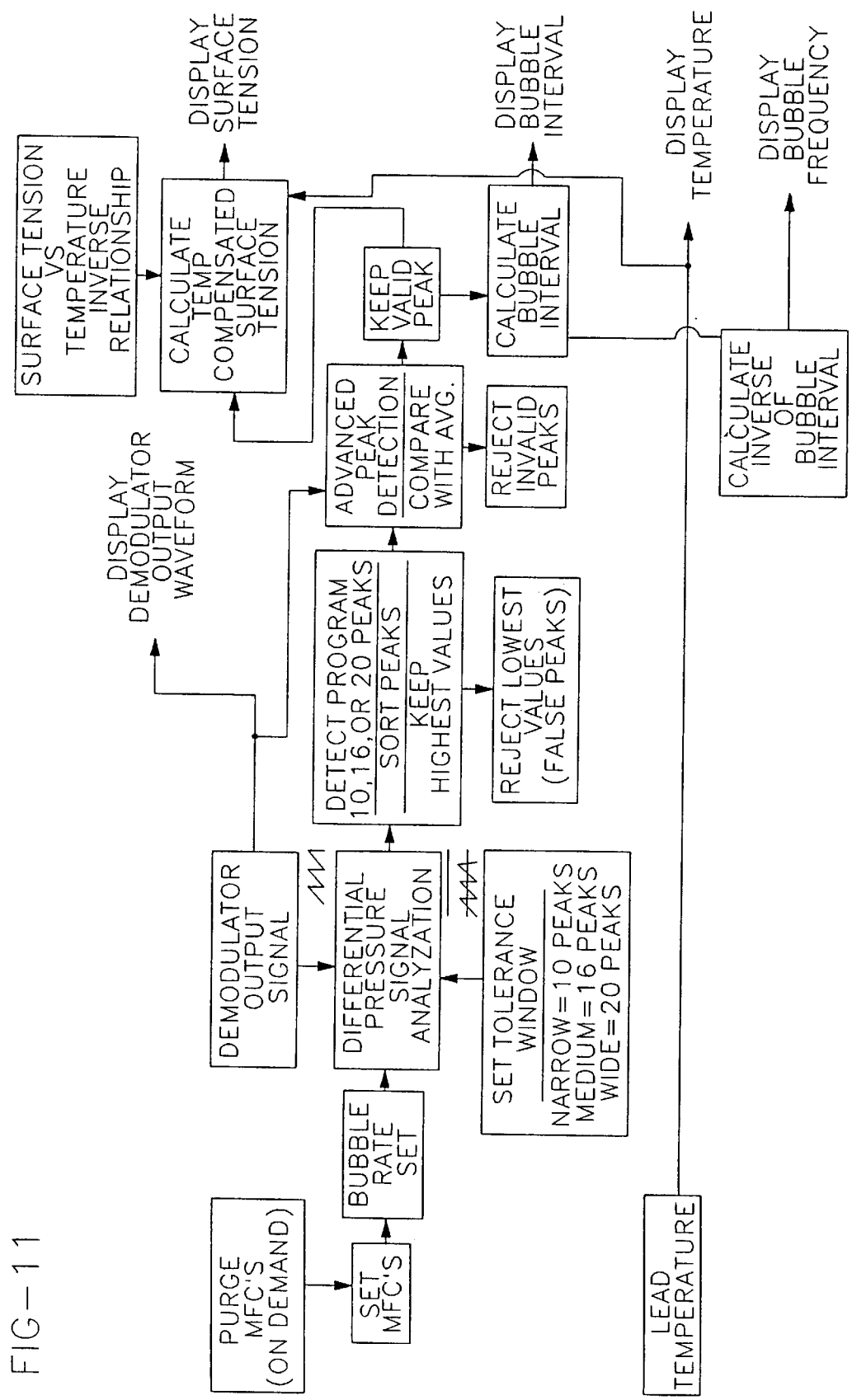
FIG. 11 is a system block diagram showing the process for measuring surface tension using the components of FIG. 1.

The output of each mass flow controller (6, 7), illustrated in FIGS. 1 and 11, is connected to a differential pressure transducer (10), Model DP15 manufactured by Validyne Engineering Sales Corporation, through a tee fitting (19); the negative (−ve) port of which is connected to the small orifice side and the positive (+ve) port of which is connected to the large orifice side.

In the case of FIGS. 2 and 12, the two transducer, viscosity compensating configuration, each orifice is connected to the −ve port with each +ve transducer port tied together and connected to the third mass flow controller (8), using a cross fitting (18) and then vented to the pressure reactor atmosphere through an open vent fitting (17) or a third tube.

The outputs of the surface tension apparatus are connected to pressurized tubing sections (20) that run to the reactor probe assembly, using high pressure tube fittings (21)

welded to the top of the flange (22). The flange is designed for, and applicable to, the particular vessel, reactor, or process pipe. The small and large orifice probes are similarly connected and suspended from similar flange-welded tube fittings (21) on the underside of the flange and supported from lengths of commercially available, fractional size, tubing (23), typically 0.25" or 6 mm. O.D. These tubes are housed within an elongated, perforated, protective rigid pipe or tube (24), threaded into a half coupling welded to the underside of the flange, that allows varying the total length and therefore the depth of penetration of the probes in the fluid by varying the length of the external pipe section and the internal connecting tubes, to suit the particular application. This arrangement is suitable for top or bottom installation, and side installation with minor modifications.

A protective, ventilated or perforated, closed end "basket" arrangement (24), threaded onto the end of the protective pipe section through a standard pipe coupling (25), mitigates the effect of shearing or turbulence from the flow or mixing of the fluid in the vessel, reactor, or pipe, while at the same time allowing the free, non-turbulent flow of the fluid past the tension orifices and associated temperature (15), or other measurement probe. Additional internal tubing spacers (26) provide rigidity to the system within the external pipe assembly and prevent movement of the probes within protective basket.

Standard tube fittings (27) allow replacement and interchange of probes and probe materials, including, but not limited to, glass, stainless steel, coated glass and steel, as well as straight or inverted probes. The tubing is pressure sealed, particularly for temperature and other process measuring probes so as to prevent fluid ingress into the probes and associated electrical wiring. The entire assembly is modular in nature for ease of assembly and disassembly for replacement and cleaning between process or production runs.

The temperature probe (15) is provided to sense temperature of the liquid under test since surface tension of a liquid is temperature dependent in an inverse relationship. As temperature of the liquid goes up, surface tension decreases. An algorithm for surface tension versus temperature relationship for two standard calibration fluids is included in the software, so that during the calibration sequence the computer program reads the temperature of the calibration fluid being used and automatically inputs the correct surface tension value. Typical standard calibration fluids are deionized water and ethyl alcohol. This algorithm can also be used to temperature compensate surface tension values during operation.

Figure 10:
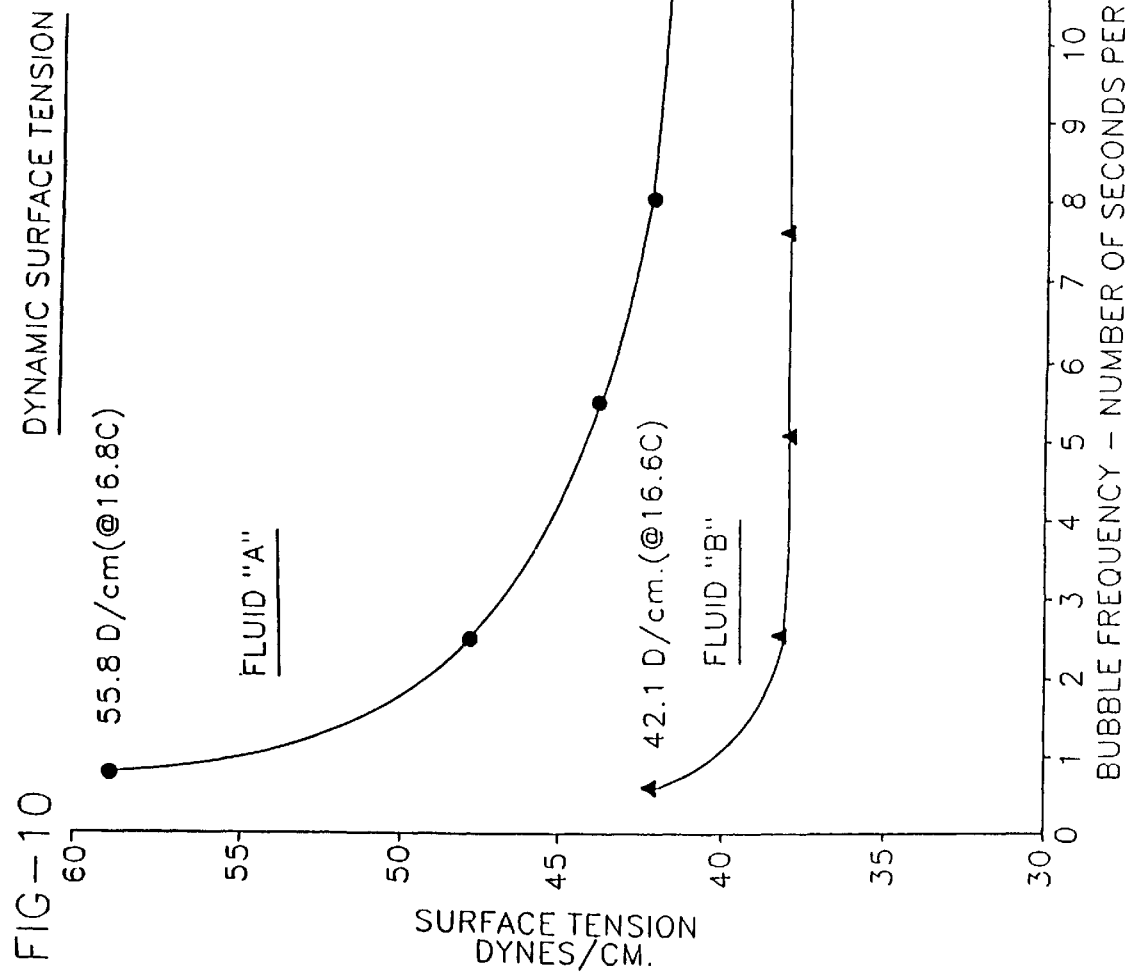
FIG. 10 is a dynamic surface tension plot for two different fluids.

The software program incorporates a sequential automatic flow control setting/calibration sequence that allows the automatic generation of dynamic surface tension curves for tested fluids that contain active surfactants (FIG. 10). The mass flow controllers are pre-programmed to sequence through a series of flow controller setting (i.e. 10, 20, 30, 40, and 50 percent of full rating, for example) which result in five different and sequentially increasing bubble rates. First the probes are immersed in a high standard calibration fluid (deionized water) and the program sequences through the different flow settings in a step-by-step procedure, pausing a sufficient period of time to allow analyzation of the differential pressure waveforms and the automatic input of the correct surface tension value for the high standard calibration fluid. This is repeated for the low standard calibration fluid (ethyl alcohol). Various test fluids are subsequently measured at these different flow rates and the resultant surface tension and bubble frequency data is plotted to give accurate dynamic surface tension curves (FIG. 10).

A power supply (9) provides operational power to the mass flow controller's. The mass flow controller input and output control signals are routed, with analog input and output control signals from transducer demodulator circuits (12), the temperature probe (15), and other sensors, to analog input and output interface boards (14) located in the computer (13) for processing by the software program. Since there is a maximum practical distance that the apparatus can be mounted away from the probe assembly and still retain signal sensitivity and desired accuracy, remote control of the apparatus and mass flow controllers is important in hazardous and explosive gas environments. A specific example is application of the apparatus to monitor and control a polyvinyl chloride (PVC) polymerization reactor using combustible, vinyl chloride gas in the reaction process. For this and similar applications, the apparatus is mounted in an explosion-proof housing, and/or in a nitrogen purged enclosure, as may be required by local safety codes and/or standards.

The equipment arrangement in FIG. 2 allows correcting for viscosity effects. An estimation of the hydrodynamic resistance of a fluid against a moving bubble is done using Stokes law for a viscous resistance of a liquid. The correction value to calculated surface tension value, which is the difference between measured value of dynamic surface tension and the real value, is estimated by the following relationship $$\Delta \gamma = \frac{3\mu r}{2\tau}$$

where:

$\mu$ is the viscosity of the liquid, $\gamma$ is the surface tension of the liquid, r is the radius of the orifice, $\tau$ is the surface age.

Since the change in surface tension occurs at both the large and the small orifice, this relationship can be reduced to a simple relationship of the radius of each of the orifice and the surface age of each bubble being formed. The bubble rate, and therefore the surface age, can be adjusted to cancel out the viscosity effect by setting the surface age of each orifice in inverse relationship to the radii of the two orifices as follows:

$$\frac{3\mu r_1}{2\tau_1} = \frac{3\mu r_2}{2\tau_2} \Rightarrow \frac{r_1}{\tau_1} = \frac{r_2}{\tau_2}$$

where $r_1$ is the small orifice radius and $r_2$ is the large orifice radius.

An advanced software peak detection program was developed to mitigate the problems encountered when using the hardware peak detection, and to give accurate surface tension measurements without false triggering of the peak detector in both ambient and pressurized environments. See FIGS. 11 and 12. This advanced software peak detection program has the means to measure the maximum bubble pressure from a demodulator output signal that can be either unipolar or bipolar (both positive, or positive and negative). It can measure fluids under pressure, with provisions to reject false peaks caused by capillary action and other oscillations. It can measure surface tension with provisions to reject false peaks in very viscous fluids, and correct for viscosity effects, both in ambient and pressurized conditions.

Figure 8:
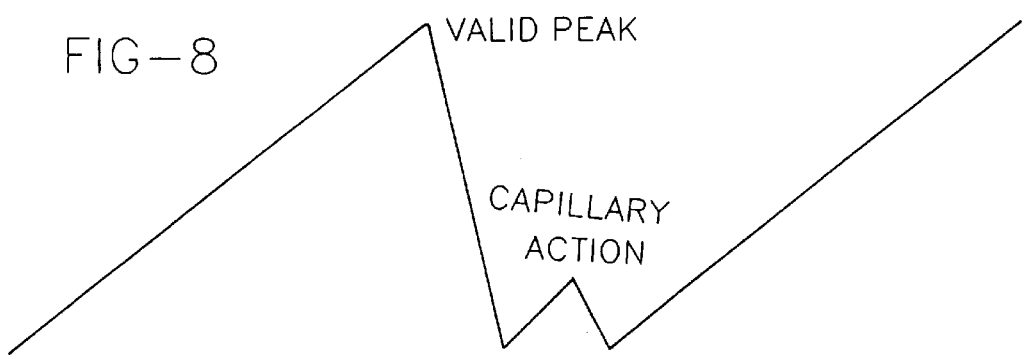
FIG. 8 is an idealized pressure waveform showing a valid and false peak due to a capillary action.

Standard software peak detection techniques cannot distinguish between valid peaks and peaks that are caused by noise (FIG. 8). Therefore, it was necessary to develop this extension to the standard software peak detection. The new advanced software peak detection algorithm uses the average of all valid peaks to compare each newly detected peak to it. Therefore, it has the ability to evaluate each newly detected peak as being valid or invalid. The user of the software has been given the flexibility to influence this detection by selecting the degree to which detected peaks are accepted as valid.

The system consists of two main parts, which are themselves divided into sub-systems (FIG. 13 through FIG. 18). The two main parts are: (1) Differential pressure signal analyzation, and (2) Differential pressure signal peak detection.

Directly after the program starts, or when the probes are immersed into a new sample, there is no average available to which the detected peaks can be compared to. Therefore, the signal has to be analyzed, meaning the standard software peak detection is used to detect a certain number of peaks. With these peak values the correct average can be determined, and is used from this point on in the advanced peak detection algorithm.

The differential pressure signal is represented in the computer by individual integral numbers. See FIGS. 14A and 14B. Eight consecutive numbers make up a detection group. See FIG. 16. Out of each detection group, the maximum and minimum values are determined, also, their indices in the memory buffer are stored. The maximum values are used to detect peaks in this algorithm in the following described procedure.

Figure 7:
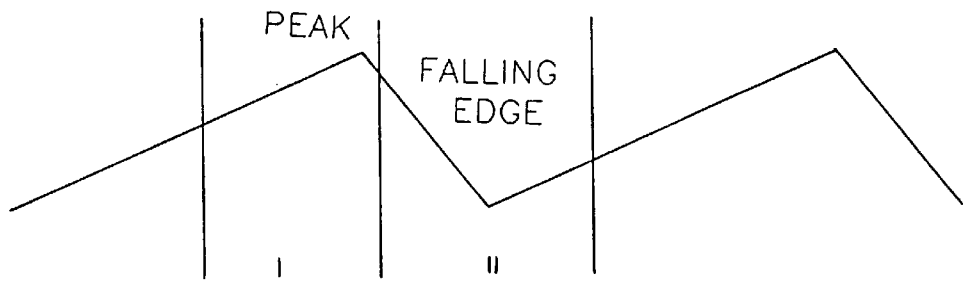
FIG. 7 is an idealized pressure waveform showing the normal peak and falling edge that occurs as each bubble forms and is released at an orifice.

To detect a peak, the falling edge of the differential pressure signal has to be detected first. A falling edge (FIG. 7) is defined by:

1. The difference between maximum and minimum value has to be higher than 366 mV (+150 integral), to avoid detection of noise peaks.

2. The index of the minimum value has to be higher than the index of the maximum value, i.e. the minimum value has to appear after the maximum value in the same detection group.

The maximum value out of the current detection group is compared to the maximum value out of the preceding detection group. This is an important step, as well as a unique feature to this algorithm during peak detection, as the peak can appear in a detection group I (FIG. 7) but the falling edge is detected in detection group II. Using this condition, it is verified that a highly accurate peak value is delivered by the peak detection algorithm.

During signal analyzation, the software tries to detect a certain number of peaks. See FIGS. 15A and 15B. This number depends on the tolerance window settings. The relation between tolerance window setting and number of analyzation peaks is:

Tolerance window NARROW—10 peaks

Tolerance window MEDIUM—16 peaks

Tolerance window WIDE—20 peaks

After the necessary number of peaks are detected and stored, the peaks are sorted by value, in this case by using the bubble sort algorithm (FIG. 17). This algorithm is not restricted to one sorting method. After the sort, the highest value in the analyzation array is in the top of the buffer, the lowest in the bottom.

EXAMPLE

| Index | Before | After |
|-------|--------|-------|
| 0 | 1.85 | −0.144 |
| 1 | 4.38 | 0.591 |
| 2 | 0.591 | 1.19 |
| 3 | 4.31 | 1.26 |
| 4 | 1.19 | 1.85 |
| 5 | 4.32 | 4.31 |
| 6 | −0.144 | 4.32 |
| 7 | 4.32 | 4.32 |
| 8 | 1.26 | 4.38 |
| 9 | 4.39 | 4.39 |

After the values are sorted, out of the five highest values, (Index 5 through 9) the correct peak average is calculated. Independently from the tolerance window setting, the five highest values are always used for the average calculation. This is derived from a differential pressure signal that consists of valid peaks and peaks from capillary actions (invalid peaks). This case can be considered the worst case, as there are an even number of valid, high peaks, and invalid, low peaks. By considering only the upper part of the analyzation array, only the valid peak values are used for the average calculation. This concludes the analyzation.

During advanced peak detection, after a peak has been detected, there has to be further examination of this value to evaluate if it is valid under the current circumstances. This evaluation makes this peak detection algorithm advanced. See FIGS. 14A and 14B.

The detected peak value is compared to the current average of all the previous valid peak values. For this comparison, a so-called tolerance window is applied. To compare the detected peak value to the current peak value average, the absolute value of the difference of peak value and peak average must be lower than the tolerance value:

$$ABS(peak_{13}\ value - peak_{13}\ average) <= tolerance\_value$$

If the result of this equation is True, the peak can be accepted as valid. In this case, the new result for surface tension can be calculated.

The user adjustable tolerance window is a very unique feature of this software. See FIGS. 8 and 9. With this window, two things are now possible:

1. Peaks that are caused by capillary actions can be rejected, so that they have no effect on the surface tension results.

2. It is possible to measure fluids of high viscosity, which have typically inconsistent differential pressure signals.

Peaks caused by capillary action have typically a peak value that is about 20% of that of peaks that appear when a bubble releases (FIG. 8).

Figure 9:
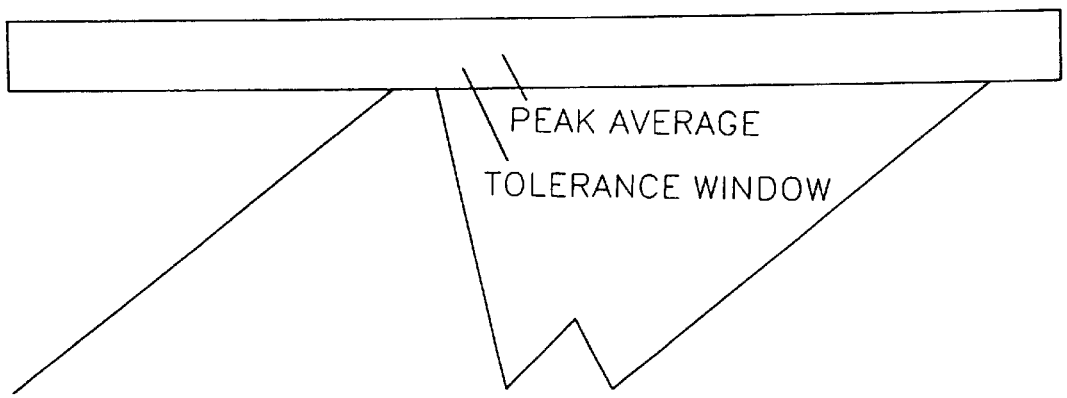
FIG. 9 is an idealized pressure waveform shooing the peak average of the software peak detection algorithm and the tolerance window.

With a standard peak detection algorithm, these two peaks cannot be differentiated, causing incorrect results for surface tension, as well as for bubble frequency. With advanced peak detection, applying the tolerance window, peaks can be differentiated (FIG. 9). The tolerance window is a value range of ±tolerance around the peak average. The valid peak that is within the tolerance window can be accepted while the capillary action is rejected.

To measure fluids with high viscosity even using the basic (FIG. 1) apparatus, the user can adjust this tolerance window to Narrow (±300 mV)

Medium (±650 mV)

Wide (±1000 mV)

Since peak values of fluids typically fluctuate more than those of a non-viscous fluid, with the adjustable tolerance window the user can determine which peaks are accepted, leading to a very accurate result for viscous fluids. Additionally, the averaging factor for the result calculation is increased with wider tolerance windows so that even with fluctuating peak values, a high stability of results can be expected.

Through a new averaging algorithm that is used in this software, two goals are achieved: (1) higher stability of results compared to moving average; and (2) faster calculation of new average. See FIGS. 18A and 18B.

For this averaging algorithm the averaging factor is introduced. The average of a certain result (either surface tension, temperature or bubble frequency) is calculated by:

$$new\_average = \frac{current\_average \cdot averaging\_factor}{averaging\_factor + 1}$$

The relation between tolerance window setting and number of analyzation peaks is:

Tolerance window NARROW—averaging factor=10
Tolerance window MEDIUM—averaging factor=21
Tolerance window WIDE—averaging factor =33

This invention provides an apparatus for determining surface tension of a liquid independent of the pressure environment of the container holding the liquid or the depth of immersion of the probes under the surface of the liquid.

This invention provides a software and hardware means to open the mass flow controller control valve to its full open position to increase the flow through the mass flow controller to a maximum, in order to purge the probes during the period that a vessel, reactor, or pipe is pressurized, so as to prevent the back flow of liquid into the probes, particularly fluids with high solids concentration that can cause plugging of the probes. This purging capability can also be used as a means to unplug the probes during the normal production cycle, if needed, as can be appreciated from the incorporation of purging as the initial step in both FIGS. 11–12.

While the form of apparatus herein described constitutes a preferred embodiment of this invention, it is to be understood that the invention is not limited to this precise form of apparatus and that changes may be made therein without departing from the scope of the invention, which is defined in the appended claims.

What is claimed is:

1. An apparatus for determining the surface tension of a liquid comprising a vessel, reactor, or process pipe system for containing a liquid under pressure;

a pair of tubes having orifices of different diameters positioned below the surface of the liquid in said vessel, reactor, or pipe system;

means for adjusting the depth of immersion of the said orifices in the liquid;

means for providing a source of gas pressure to said tubes using a separate mass flow controller for each tube;

means connected between said source of gas and said tubes for providing a regulated, constant volume flow rate of gas to the tubes independently of pressure inside the vessel, reactor, or pipe system;

means for automatically controlling the flow of gas to the tubes and therefore the bubble rate of gas at the orifices independent of the pressure inside said vessel, reactor, or pipe system;

means for measuring the maximum differential pressure of the bubbles forming at the probes as a function of the surface tension of the liquid, using a differential pressure transducer;

means to measure the temperature of a standard calibration fluid and automatically calculate the correct temperature compensated surface tension value;

means to automatically sequence the flow controller settings and generate dynamic surface tension curves using a sequential flow-control setting/calibration sequence.

2. An apparatus for determining the surface tension of a liquid comprising means to automatically control the bubble rate through a tube immersed in a vessel, reactor, or section of process pipe, independent of the pressure inside said vessel, reactor, or pipe, or the depth of immersion;

means to purge said tube during startup and operation;

means to measure the maximum bubble pressure signal from a demodulator output circuit that can be either unipolar or bipolar;

means to measure the maximum bubble pressure, and therefore the surface tension of a liquid with provisions to reject false peaks caused by capillary action independent of the pressure environment of the liquid;

means to measure the maximum bubble pressure, and therefore the surface tension of a liquid with provisions to reject false peaks caused by oscillations in the maximum bubble pressure waveform independent of the pressure environment of the liquid;

means to measure surface tension in a viscous fluid with provisions to reject false peaks due to fluctuations of the differential pressure waveform caused by the hydrodynamic resistance of the viscous fluid against bubbles being formed at the orifice;

means to automatically measure the temperature of a standard calibration fluid and choose the correct temperature compensated surface tension value;

means to automatically sequence the flow controller settings and generate dynamic surface tension curves using a sequential flow-control setting/calibration sequence.

3. An apparatus for determining the surface tension of a liquid comprising means to automatically control the bubble rate through two tubes immersed in a vessel, reactor, or section of process pipe independent of the pressure inside said vessel, reactor or pipe or depth of tube immersion;

means to purge said tubes during startup and operation;

means to measure the maximum bubble pressure signals from demodulator output circuits that can be either unipolar or bipolar;

means to measure the maximum bubble pressure and therefore the surface tension of a liquid with provisions to reject false peaks caused by capillary action independent of the pressure environment of the liquid;

means to measure the maximum bubble pressure at an orifice and average peaks caused by oscillations in the maximum bubble pressure waveform in a pressurized environment and therefore determine the surface tension of the liquid;

means to measure surface tension in a viscous fluid with provisions to reject false peaks due to fluctuations of the differential pressure waveform caused by the hydrodynamic resistance of the viscous fluid to a bubble being formed at the orifice;

means to automatically measure the temperature of a standard calibration fluid and calculate the correct temperature compensated surface tension value;

means to automatically sequence the flow controller settings and generate dynamic surface tension curves using a sequential flow-control setting/calibration sequence.

4. An apparatus for determining the surface tension of a liquid comprising means to automatically control the bubble rate through two or more tubes with different orifice sizes immersed in a vessel, reactor, or section of process pipe independent of the pressure inside said vessel, reactor or pipe or depth of immersion in the liquid;

means to purge said tubes at any time during startup and operation;

means to measure the maximum bubble pressure signals from demodulator output circuits that can be either unipolar or bipolar;

means to measure the maximum bubble pressure, and therefore the surface tension of a liquid with provisions to reject false peaks caused by capillary action independent of the pressure environment of the liquid;

means to measure the maximum bubble pressures independently at two orifices and reject false peaks caused by oscillations in the maximum bubble pressure waveforms in a pressurized environment, with means to subtract the resulting maximum bubble pressure values to determine the differential and thereby determine the surface tension of the liquid;

means to measure the maximum bubble pressure independently at each of two orifices in a viscous liquid and means to set the flow rates at each orifice in a ratio that will cancel the effect of the hydrodynamic resistance of the viscous fluid to bubbles being formed at the orifices;

means to automatically measure the temperature of a standard calibration fluid and choose the correct temperature compensated surface tension value;

means to automatically sequence the flow controller settings and generate dynamic surface tension curves using a sequential flow-control setting/calibration sequence.

5. In an apparatus for determining the surface tension of a liquid including at least two tubes (2,3) having orifices of different diameters positioned below the surface of a liquid in a vessel, reactor, or section of process pipe;

means for providing a source of gas (4) to said tubes;

means connected between said source of gas and tubes (6, 7) for providing a regulated, constant volume flow rate of gas to the tubes;

means for controlling the flow of gas to the probes (13) and therefore the bubble rate at the orifices; and means for measuring the maximum differential pressure of the bubbles forming at the probes as a function of the surface tension of the liquid, using a differential pressure transducer (10);

the improvement characterized by means for adjusting the depth of immersion of the said orifices in the liquid (24);

wherein said means for providing a source of gas pressure to said tubes includes a separate mass flow controller (6, 7) for each tube;

means to automatically measure the temperature (15) of a standard calibration fluid and to calculate the correct temperature compensated surface tension value; and means to automatically sequence (13) the flow controller settings and generate dynamic surface tension curves using a sequential flow-control setting/calibration sequence.

6. The apparatus of claim 5 further comprising a vessel, reactor, or process pipe system for containing a liquid under pressure;

means connected between said source of gas and said tubes for providing a regulated, constant volume flow rate of gas to the tubes independently of pressure inside the vessel, reactor, or pipe system; and means for automatically controlling the flow of gas to the tubes and therefore the bubble rate of gas at the orifices independent of the pressure inside said vessel, reactor, or pipe system.

7. An apparatus of claim 6 further comprising a third mass flow controller vented to the vessel atmosphere or to a third tube to offset the pressure inside the vessel, reactor, or pipe system;

means for measuring the maximum differential pressure of the bubbles forming at the probes as a function of the surface tension of the liquid, using two or more differential pressure transducers with one common side connected to the pressurized system inside said vessel, reactor, or pipe system.

8. In an apparatus for determining the surface tension of a liquid comprising at least two tubes having orifices of different diameters positioned below the surface of a liquid in a vessel, reactor, or section of process pipe;

means for providing a source of gas to said tubes;

means connected between said source of gas and tubes for providing a regulated, constant volume flow rate of gas to the tubes;

means for controlling the flow of gas to the probes and therefore the bubble rate at the orifices; and means for measuring the maximum differential pressure of the bubbles forming at the probes as a function of the surface tension of the liquid, using a differential pressure transducer;

the improvement characterized by means to automatically control the bubble rate through a tube immersed in a vessel, reactor, or section of process pipe, independent of the pressure inside said vessel, reactor, or pipe, or the depth of immersion;

means to purge said tube during startup and operation;

means to measure the maximum bubble pressure signal form a demodulator output circuit that can be either unipolar or bipolar;

means to measure the maximum bubble pressure and therefore the surface tension of a liquid using automatic mass flow controllers that allow a predictable differential pressure signal to be generated, means responsive to said differential pressure signal for rejecting false maximum bubble pressure signals due to fluctuations of the differential pressure waveform caused by the hydrodynamic resistance of the viscous fluid against bubbles being form at the orifice;

means to automatically measure the temperature of a standard calibration fluid and choose the correct temperature compensated surface tension value;

means to automatically sequence the flow controller settings and generate dynamic surface tension curves using a sequential flow-control setting/calibration sequence.

9. The apparatus of claim 8 further comprising means to measure the maximum bubble pressure, and therefore the surface tension of a liquid with provisions to reject false peaks caused by capillary action independent of the pressure environment of the liquid; and means to measure the maximum bubble pressure at an orifice and to average the peaks caused by oscillations in maximum bubble pressure waveform in a pressurized environment and therefore determine the surface tension of the liquid.

10. The apparatus of claim 9 further comprising means to measure the maximum bubble pressures independently at two orifices and reject false peaks caused by oscillations in the maximum bubble pressure wave forms in a pressurized environment, with means to subtract the resulting maximum bubble pressure value to determine the differential and thereby determine the surface tension of the liquid;

means to measure the maximum bubble pressure independently at each of two orifices in a viscous liquid and means to set the flow rates at each orifice in a ratio that will cancel the effect of the hydrodynamic resistance of the viscous fluid to bubble being formed at the orifices; and means to automatically measure the temperature of a standard calibration fluid and choose the correct temperature compensated surface tension value.

* * * * *

UNITED STATES PATENT AND TRADEMARK OFFICE
CERTIFICATE OF CORRECTION

PATENT NO : 6,085,577
DATED : July 11, 2000
INVENTOR(S): Tanya C. Christensen, et al It is certified that error appears in the above-identified patent and that said Letters Patent are hereby corrected as shown below:

Column 4, line 1, the word "shooing" should be "showing"

line 9, insert the word "tension" after the word "surface"

Claim 8, at column 12, line 54 where "form" should be "formed"

Claim 10, column 14, line 11 the word "bubble" should read "bubbles"

In the Drawings

Fig. 11 - lower left-hand corner the notation in the box should be "READ TEMPERATURE" not "LEAD TEMPERATURE"

Figure 14B:
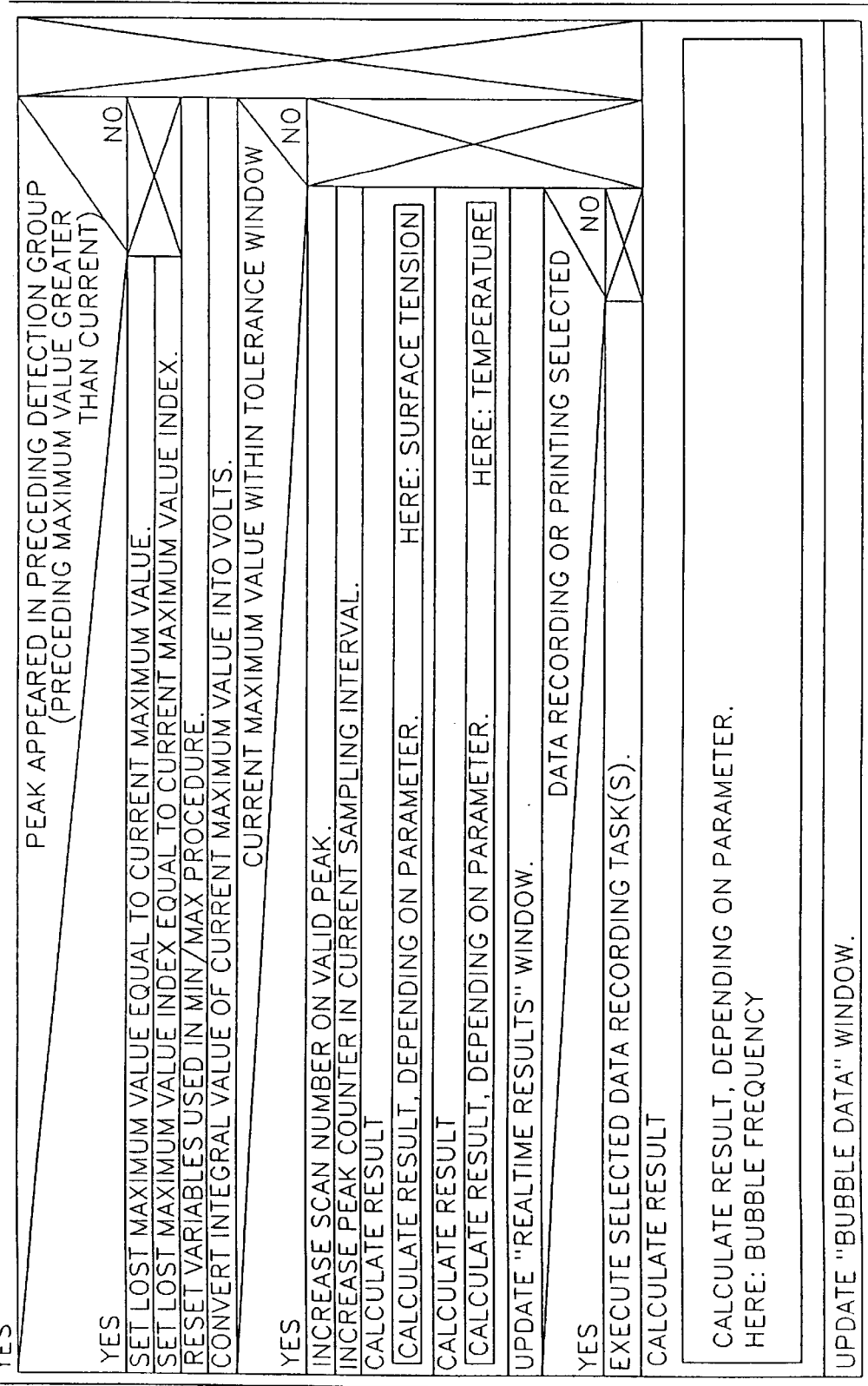
Figure 15A:
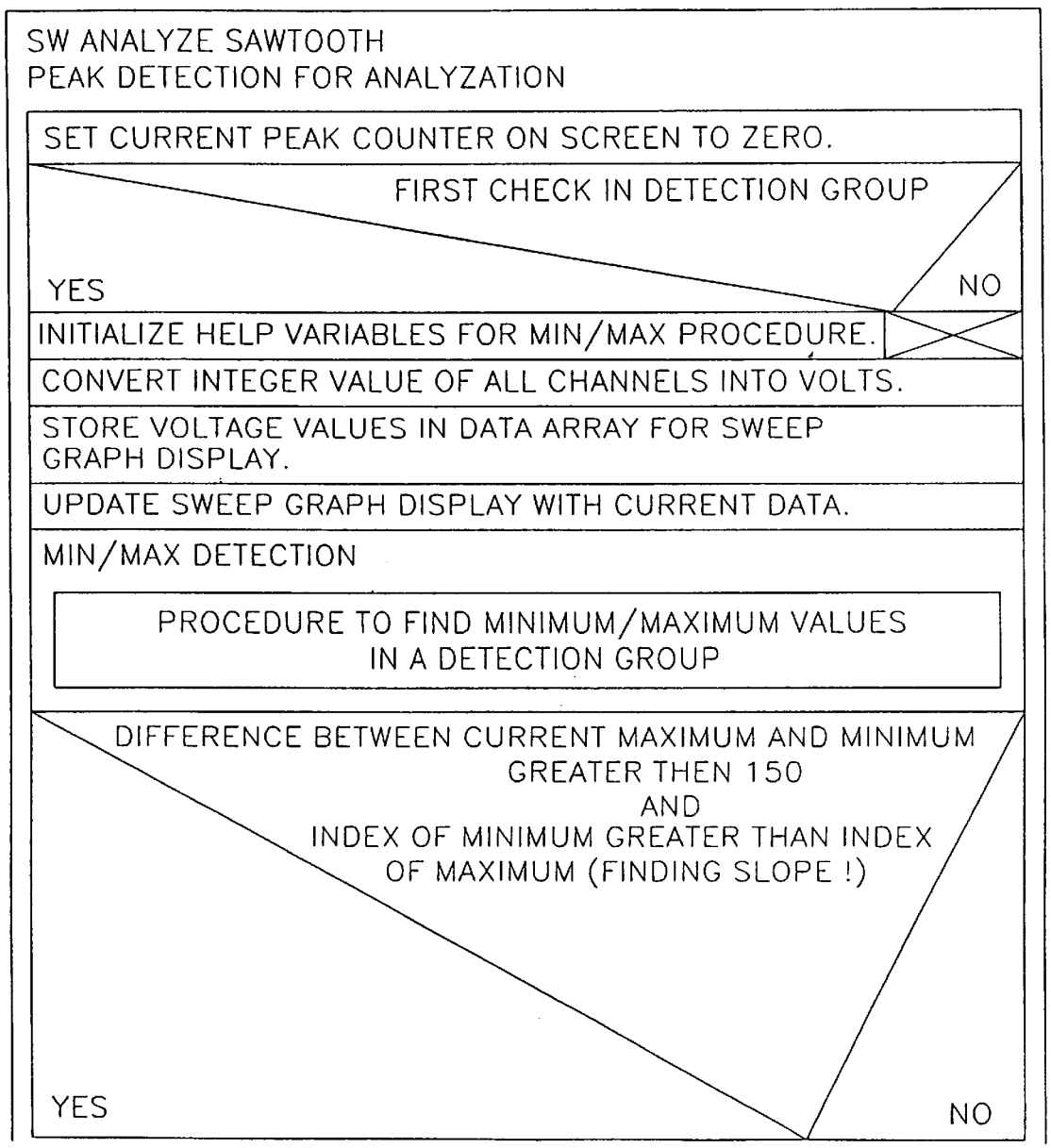
FIGS. 15A, 15B and 15C together comprise a software flow diagram of a software routine for detecting peak signals during bubbling.
Figure 15B:
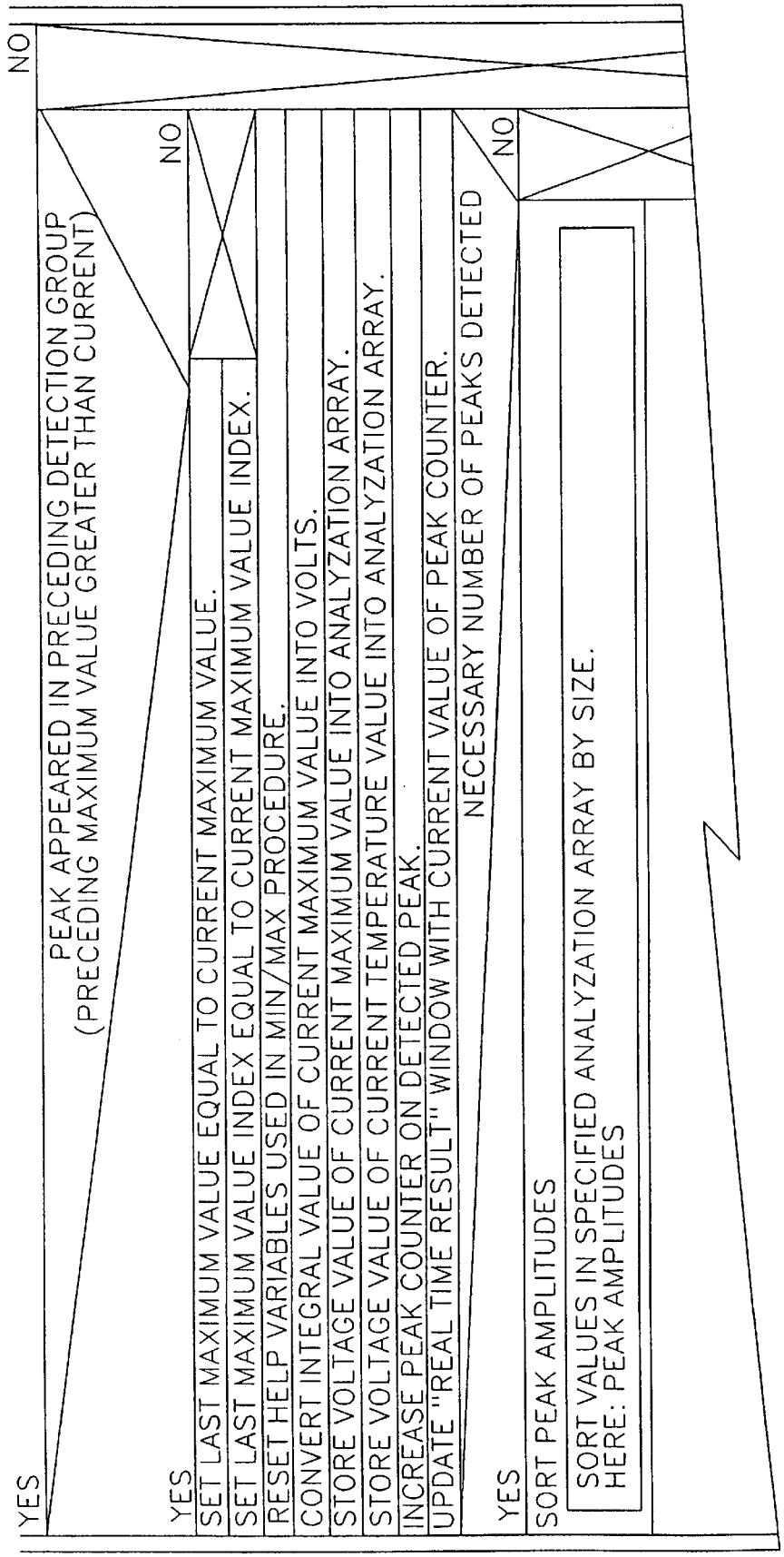
Figure 15C:
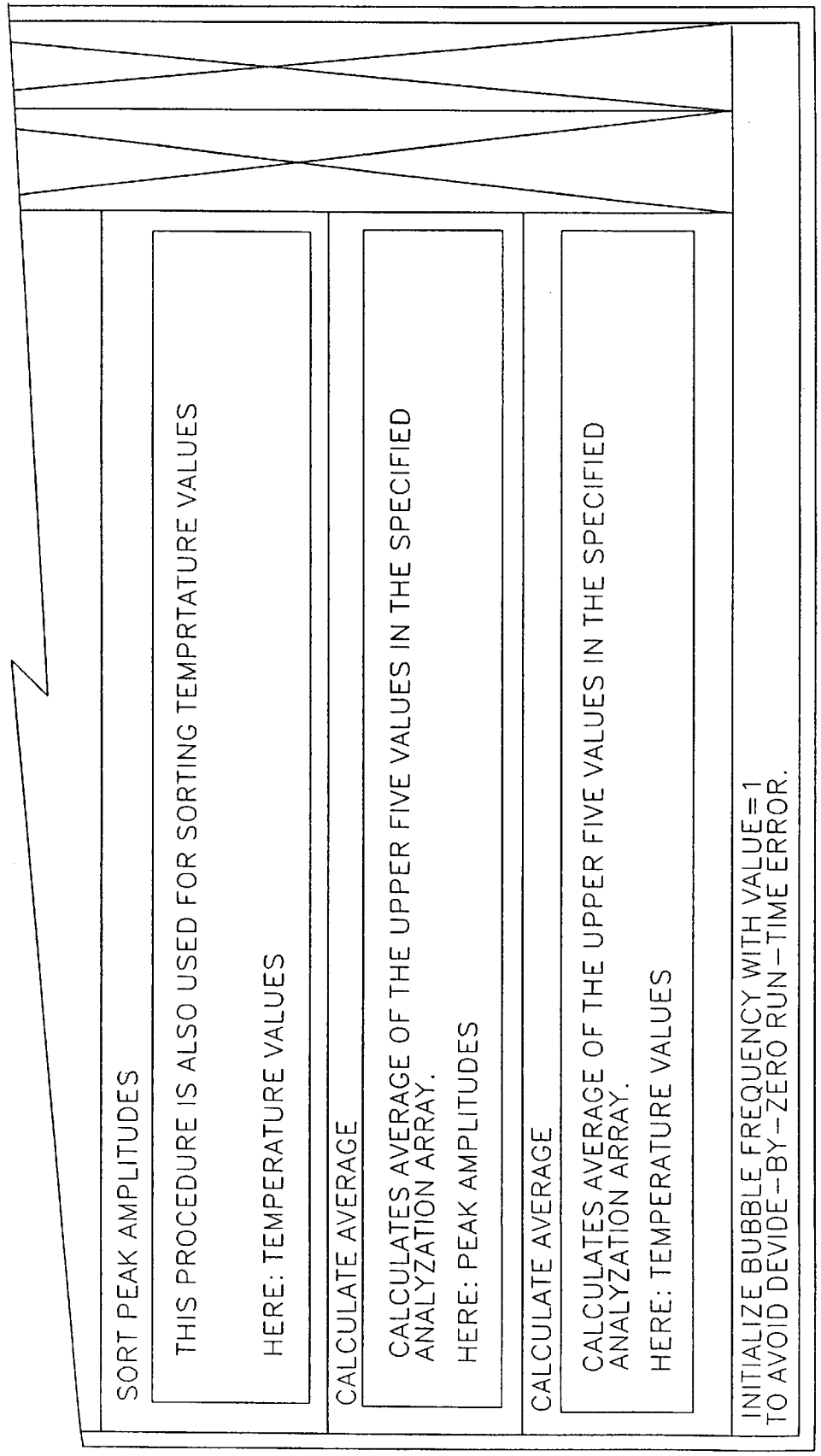
Figure 16:
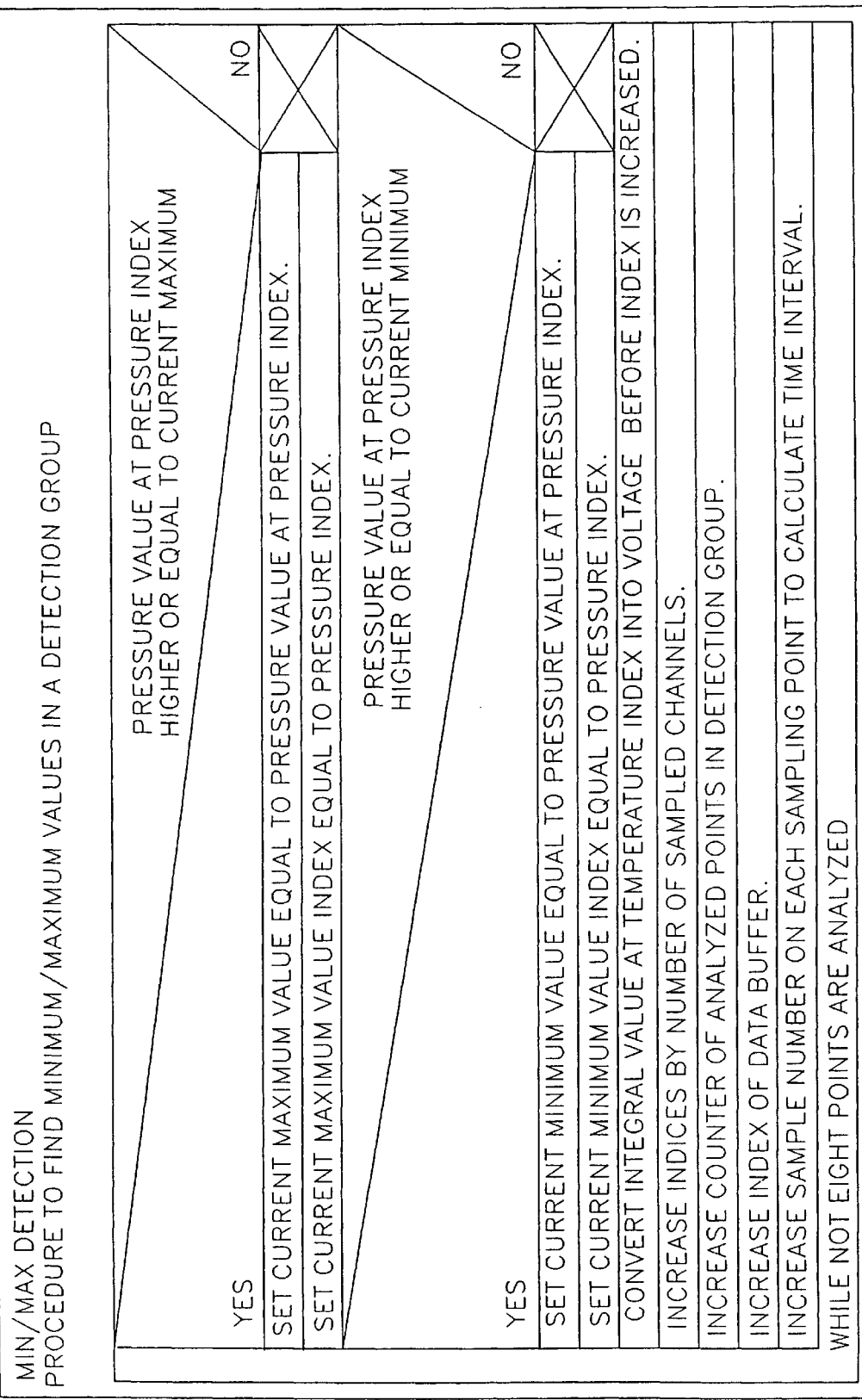
FIG. 16 is a software flow diagram for detecting maximum and minimum values in a detection group.
Figure 18A:
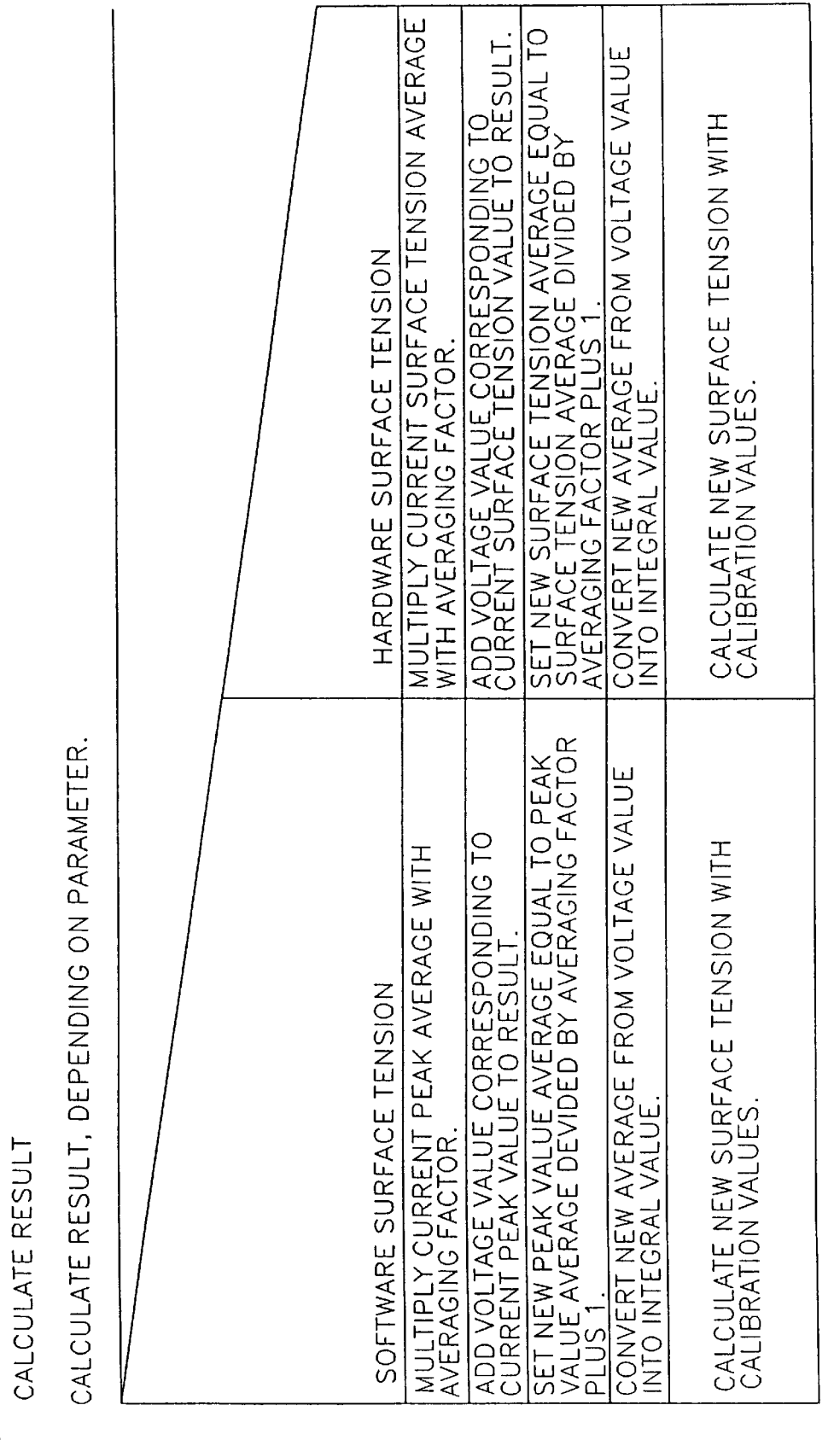
FIGS. 18A and 18B together comprise a software routine for calculating the results of the surface tension measurement.
Figure 18B:
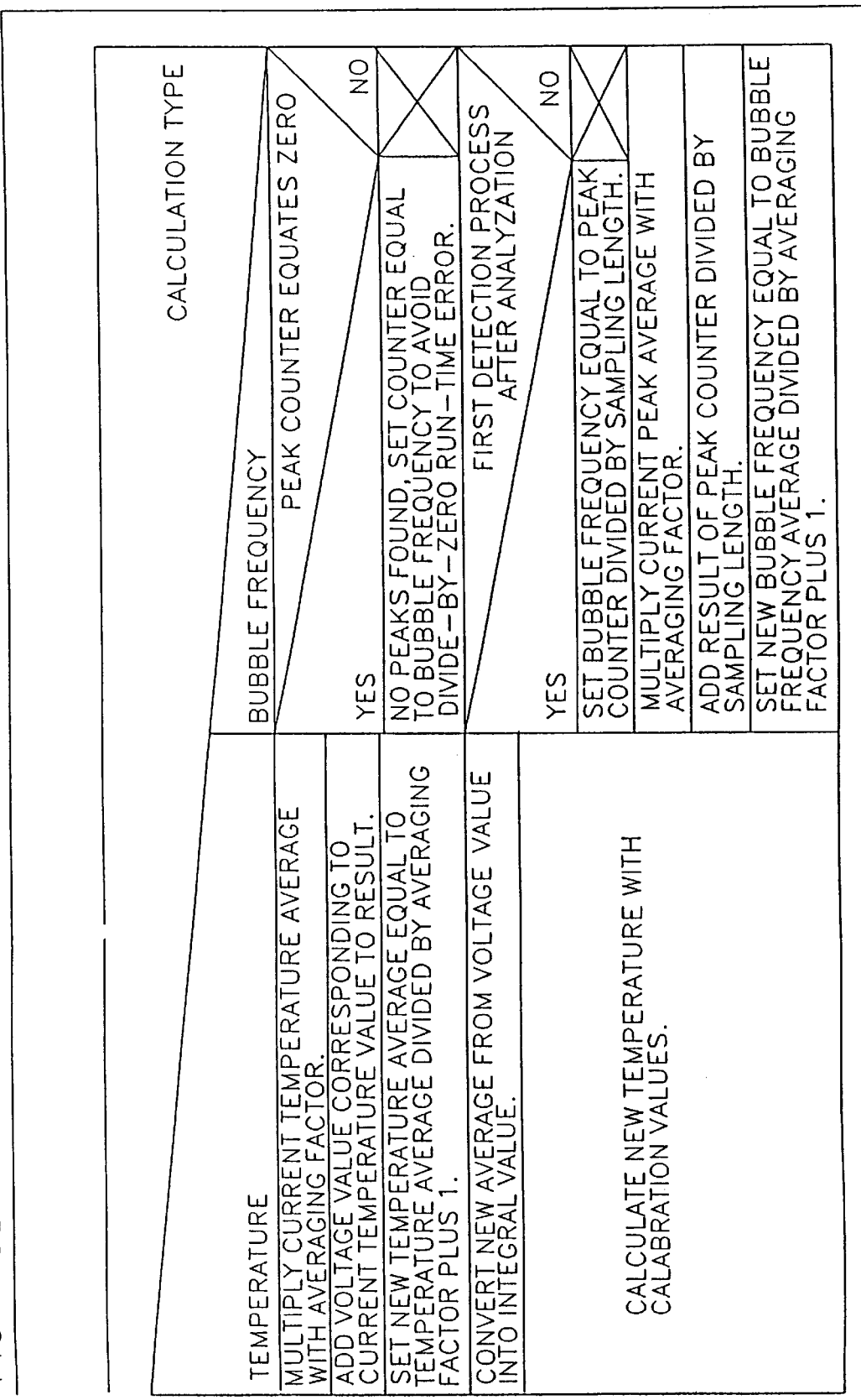

Fig. 14b - upper left-hand corner after each occurrence of "SET" should be "LAST"

UNITED STATES PATENT AND TRADEMARK OFFICE
CERTIFICATE OF CORRECTION

PATENT NO : 6,085,577
DATED : July 11, 2000
INVENTOR(S): Tanya C. Christensen, et al It is certified that error appears in the above-identified patent and that said Letters Patent are hereby corrected as shown below:

In the Abstract

Line 2, where "(2)" should be "(1)"

Line 4, where "100" should be "1000"

Line 31, where "transdcuer" should be "transducer"

Signed and Sealed this

Twenty-fourth Day of April, 2001

Attest:

NICHOLAS P. GODICI

Attesting Officer

Acting Director of the United States Patent and Trademark Office